(12) United States Patent
Lin et al.

(10) Patent No.: US 11,752,215 B2
(45) Date of Patent: Sep. 12, 2023

(54) TARGETING TUMOR CELLS WITH CHEMOTHERAPEUTIC AGENTS CONJUGATED TO ANTI-MATRIPTASE ANTIBODIES BY IN VIVO CLEAVABLE LINKING MOIETIES

(71) Applicants: Rutgers, The State University of New Jersey, New Brunswick, NJ (US); Georgetown University, Washington, DC (US)

(72) Inventors: Siang-Yo Lin, East Brunswick, NJ (US); Joseph R. Bertino, Branford, CT (US); Chen-Yong Lin, Falls Church, VA (US); Zoltan Szekely, New Brunswick, NJ (US)

(73) Assignees: RUTGERS, THE STATE UNIVERSITY OF NEW JERSEY, New Brunswick, NJ (US); GEORGETOWN UNIVERSITY, Washington, DC (US)

( * ) Notice: Subject to any disclaimer, the term of this patent is extended or adjusted under 35 U.S.C. 154(b) by 19 days.

(21) Appl. No.: 17/200,136

(22) Filed: Mar. 12, 2021

(65) Prior Publication Data
US 2021/0299270 A1 Sep. 30, 2021

Related U.S. Application Data

(63) Continuation of application No. 16/085,848, filed as application No. PCT/US2017/022993 on Mar. 17, (Continued)

(51) Int. Cl.
*A61K 47/68* (2017.01)
*A61K 47/65* (2017.01)
(Continued)

(52) U.S. Cl.
CPC .......... *A61K 47/6871* (2017.08); *A61K 31/40* (2013.01); *A61K 31/4439* (2013.01);
(Continued)

(58) Field of Classification Search
None
See application file for complete search history.

(56) References Cited

U.S. PATENT DOCUMENTS

| | | |
|---|---|---|
| 5,518,888 A | 5/1996 | Waldman |
| 6,573,096 B1 | 6/2003 | Chen |

(Continued)

FOREIGN PATENT DOCUMENTS

| | | | |
|---|---|---|---|
| JP | 2009521913 A | 6/2009 | |
| JP | 2013543003 A | 11/2013 | |

(Continued)

OTHER PUBLICATIONS

Doronina et al., Nat. Biotech., 21,778-784, 2003 (Year: 2003).*
(Continued)

*Primary Examiner* — Karl J Puttlitz
(74) *Attorney, Agent, or Firm* — FOX ROTHSCHILD LLP

(57) ABSTRACT

The present invention relates to anti-matriptase antibodies and immunoconjugates of anti-matriptase antibodies with cytotoxic agents and the use thereof for killing or inhibiting the growth of matriptase-expressing cancer cells, such as those of multiple myeloma and breast cancers. In particular, immunoconjugates comprising an anti-matriptase monoclonal antibody and anticancer agents such as auristatin, including monomethyl auristatin E (MMAE) and monomethyl auristatin F (MMAF) are introduced, which have potent antitumor activity in vivo. Moreover, importantly; there was no weight loss or other evidence of toxicity in the animals, indicating that no significant free drug was released into the (Continued)

circulation from the conjugate. The present invention also provides compositions comprising these new immunoconjugates and use of them for treatment of malignancies comprising cells that express matriptase. In addition, administration of an anti-matriptase antibody or immunoconjugates of an anti-matriptase antibody and a cytotoxic agent in combination with administration of an immunomodulatory agent, such as thalidomide or an analog thereof, provides a more effective treatment of these cancers.

9 Claims, 19 Drawing Sheets

Related U.S. Application Data 2017, now abandoned, which is a continuation-in-part of application No. 15/075,008, filed on Mar. 18, 2016, now Pat. No. 9,849,192.

(51) Int. Cl.

| | |
|---|---|
| *A61K 47/60* | (2017.01) |
| *A61P 35/00* | (2006.01) |
| *A61K 31/40* | (2006.01) |
| *A61K 31/4439* | (2006.01) |
| *C07K 16/30* | (2006.01) |
| *C07K 16/40* | (2006.01) |
| *A61K 39/00* | (2006.01) |

(52) U.S. Cl.
CPC ............ *A61K 47/60* (2017.08); *A61K 47/65* (2017.08); *A61K 47/6803* (2017.08); *A61K 47/6809* (2017.08); *A61K 47/6811* (2017.08); *A61P 35/00* (2018.01); *C07K 16/30* (2013.01); *C07K 16/40* (2013.01); *A61K 2039/505* (2013.01); *C07K 2317/73* (2013.01)

(56) References Cited

U.S. PATENT DOCUMENTS

| | | | |
|---|---|---|---|
| 7,355,015 B1* | 4/2008 | Dickson | ............... A61P 17/00 424/94.1 |
| 7,572,444 B2 | 8/2009 | Foltz et al. | |
| 8,043,620 B2 | 10/2011 | Qian et al. | |
| 8,883,429 B2 | 11/2014 | Tomaskova et al. | |
| 9,849,192 B2 | 12/2017 | Lin et al. | |
| 10,376,597 B2 | 8/2019 | Lin et al. | |
| 2006/0171884 A1* | 8/2006 | Foltz | ............... A61P 35/04 424/1.49 |
| 2009/0022658 A1 | 1/2009 | Braslawsky et al. | |
| 2009/0130114 A1 | 5/2009 | Qian et al. | |
| 2009/0175873 A1 | 7/2009 | Liu | |
| 2009/0226453 A1 | 9/2009 | Herr et al. | |
| 2011/0135570 A1 | 6/2011 | Janatpour et al. | |
| 2015/0165064 A1 | 6/2015 | Bregeon et al. | |
| 2015/0250895 A1 | 9/2015 | Lin et al. | |
| 2016/0015728 A1 | 1/2016 | Lin et al. | |
| 2016/0289338 A1* | 10/2016 | Terrett | ............... A61K 47/6871 |

FOREIGN PATENT DOCUMENTS

| | | |
|---|---|---|
| JP | 2015209426 A | 11/2015 |
| WO | 1996/039183 | 12/1996 |
| WO | 0143773 A1 | 6/2001 |
| WO | 2009/020645 | 2/2009 |
| WO | 2009/114335 A2 | 9/2009 |
| WO | 2010119704 A1 | 10/2010 |
| WO | 2010138564 A1 | 12/2010 |
| WO | 2011/063127 | 5/2011 |
| WO | 2012068366 A2 | 5/2012 |
| WO | 2012/093340 | 7/2012 |
| WO | 2015075477 A1 | 5/2015 |
| WO | 2015188934 A1 | 12/2015 |

OTHER PUBLICATIONS

Jain et al., Pharm Res (2015) 32:3526-3540 (Year: 2015).*
Database Caplus Chemical Abstracts Service, Columbus, Ohio, US; CAS Registry No. 2055024-64-9; Entered STN: Dec. 28, 2016; L-Ornithinamide, N-(15-azido-1-oxo-4,7,10,13-tetraoxapentadec-1-yl)-L-valyl-N5-(aminocarbonyl)-N-[4-(hydroxymethyl)phenyl]- (CA Index Name) (Year: 2016).*
Li et al., Curr Opin Oncol. (2010) 22 (6): 579-85 (Year: 2010).*
Tageja et al., (Mar. 2011), Anti-Cancer Agents Med. Chem. (2011) 11(3): 315-26 (Year: 2011).*
Kotla et al., (Aug. 2009) J Hematol Oncol. 2:36 (Year: 2009).*
Goodman & Gilman's Manual of Pharmacology and Therapeutics Manual of Pharmacology and Therapeutics, 2008, McGraw-Hill Medical, pp. 853-861 (Year: 2008).*
Lhospice et al., Mol. Pharmaceutics 2015, 12, 1863-1871 (Year: 2015).*
Tanimoto, et al: "Transmembrane serine protease TADG-15 (ST14/Matripase/MT-SP1): expression and prognostic value in ovarian cancer", British Journal of Cancer 92: 278-283. (2005).
Lesur, et al: "Covalent linkage of anthracyclines to macromoleclar carriers", Protides of teh Biological Fluids (1985), vol. 32, pp. 437-440.
Bertino, et al: "Abstract 2596: Targeted Delivery of Doxorubicin Conjugated with Anti-Matriptase Antibody to Treat Multiple Myeloma",American Association for Cancer Research, [retrieved on Sep. 30, 2016]. Retrieved from the Internet <URL:http://cancerres.aacrjournals.org/content/70/8_Supplement/2596>> Abstract.
Lin Yong, et al: "Targeted Delivery of Doxorubicin Conjugated with Anti-Matriptase Antibody to Treat Multiple Myeloma", Proceedings of the American Association for Cancer Research Annual Meeting, Apr. 2010, Abstract only.
Doronina, et al: "Development of Potent Monoclonal Antibody Auristatin Conjugates for Cancer Therapy", Jul. 2003, Nature Biotechnology, vol. 21, No. 7, pp. 778-784.
Grewal, I.S.: "CD70 as a Therapeutic Target in Human Malignancies", Expert Opinion on Therapeutic Targets, 2008, vol. 12, pp. 341-351.
Ricart, et al: "Technology Insight: Cytotoxic Drug Immunoconjugtes for Cancer Therapy", Nature Clinical Practice Oncology, Apr. 2007, vol. 4, No. 4, pp. 245-255.
Lin C.Y., et al, "Purification and Characterization of a Complex Containing Matriptase and a Kunitz-type Serine Protease Inhibitor from Human Milk" J. Biol. Chem., 1999, 274(26): 18237-18242.
Oberst, M.D., et al, "The activation of matriptase requires its noncatalytic domains, serine protease domain, and its cognate inhibitor" J. Biol. Chem., Jul. 18, 2003, 278:26773-26779.
Oberst, M.D., et al, "HAI-1 regulates activation and expression of matriptase, a membrane-bound serine protease" Am. J. Physiol. Cell Physiol., 2005, 289:C462-C470.
Lee, S.L., et al, "Activation of hepatocyte growth factor and urokinase/plasminogen activator by matriptase, an epithelial membrane serine protease" J. Biol. Chem., 2000, 275:36720-36725.
Suzuki, M., et al, "Inhibition of tumor invasion by genomic down-regulation of matriptase through suppression of activation of receptor-bound pro-urokinase" J. Biol. Chem., Apr. 9, 2004, 279:14899-14908.
Trusolino, L. and Comoglio, P.M., "Scatter-factor and semaphorin receptors: cell signalling for invasive growth" Nat. Rev. Cancer, Apr. 1, 2002, 2:289-300.
Sidenius, N. and Blasi, F., "The urokinase plasminogen activator system in cancer: recent advances and implication for prognosis and therapy" Cancer Metastasis Rev., 2003, 22:205-222 (abstract only).
Uhland, K., "Matriptase and its putative role in cancer" Cell. Mol. Life Sci., 2007, 63(24):2968-78 (Abstract only).
Kang, J.Y., et al, "Tissue Microarray Analysis of Hepatocyte Growth Factor/Met Pathway Components Reveals a Role for Met, Matriptase,

(56) References Cited

OTHER PUBLICATIONS and Hepatocyte Growth Factor Activator Inhibitor 1 in the Progression of Node-negative Breast Cancer" Cancer Res., Mar. 1, 2003, 63: 1101-1105.

Saleem, M., et al, "A novel biomarker for staging human prostate adenocarcinoma: overexpression of matriptase with concomitant loss of its inhibitor, hepatocyte growth factor activator inhibitor-1" Cancer Epidemiol. Biomarkers Prev., Feb. 2006: 15, 217-227.

Takeuchi, N., et al, "Reverse biochemistry: Use of macromolecular protease inhibitors to dissect complex biological processes and identify a membrane-type serine protease in epithelial cancer and normal tissue" Proc. Natl. Acad. Sci. USA, Sep. 28, 1999, 96, 11054-11061.

Galkin, A.V., et al, "CVS-3983, a selective matriptase inhibitor, suppresses the growth of androgen independent prostate tumor xenografts" Prostate, Nov. 1, 2004, 61, 228-235 (Abstract only).

Chen, Y. W., et al, "Regulation of the Matriptase-Prostasin Cell Surface Proteolytic Cascade by Hepatocyte Growth Factor Activator Inhibitor-1 during Epidermal Differentiation" J. Biol. Chem., 2010, 285 (41):31755-31762.

Tolcher, A. W., et al, "Randomized phase II study of BR96-doxorubicin conjugate in patients with metastatic breast cancer" J. Clin. Oncol., Feb. 1999, 17: 478-484 (Abstract only).

Denz, U. et al, "State of the art therapy in multiple myeloma and future perspectives" Eur. J. Cancer., Jul. 2006, 42:1591-1600 (Abstract only).

Gieseler, F., "Pathophysiological considerations to thrombophilia in the treatment of multiple myeloma with thalidomide and derivates" Thromb. Haemost., Jun. 2008, 99: 1001-1007 (Abstract only).

Jain, et al: "Current ADC Linker Chemistry", Pharm Res, 2015, vol. 32, pp. 3526-3540.

Database Caplus Chemical Abstracts Service, Columbus, Ohio, US; CAS Registry No. 2055024-64-9; Entered STN : Dec. 28, 2016.

Li, et al: Recent Advances of IMiDs in Cancer Therapy, Curr Opin Oncol. 2010, vol. 22, No. 6, pp. 579-585.

Tageja, et al: "Lenalidomide—Current Understanding of Mechanistic Properties", Anticancer Agents Med Chem, Mar. 2011, vol. 11, No. 3, pp. 315-326 (Abstract).

Kotla, et al: "Mechanism of Action of Lenalidomide in Hematological Maglignancies", Journal of Hematology & Oncology, Aug. 12, 2009, vol. 2, No. 36, pp. 1-10.

Goodman & Gilman's Manual of Pharmacology and Therapeutics Manual of Pharmacology and Therapeutics, 2008, McGraw-Hill Medical, pp. 853-861.

Lloyd, et al: "Modelling the Human Immune Response: Perforamcne of a 1011 Human Antibody Repertoire Against a Broad Panel of Therapeutically Relevant Antigens", Protein Engineering, Design & Selection, vol. 22, No. 3, pp. 15-168, Oct. 29, 2008, doi; 10.1093/protein/gzn058.

Wu, et al: "Matriptase is Involved in ErbB-2-Induced Prostate Cancer Cell Invasion", Dec. 6, 2010, The American Journal of Pathology, vol. 177, No. 6, pp. 3145-3158.

Executed Declaration under 37 CFR 1.132 from Dr. Siang-Yo Lin filed on Mar. 29, 2017 in U.S. Appl. No. 15/075,008 (6 pages).

Executed Declaration under 37 CFR 1.132 from Dr. Siang-Yo Lin filed on Jul. 20, 2016 in U.S. Appl. No. 14/835,881 (6 pages).

Lee et al: "Autoactivation of matriptase in vitro: requirement for biomembrane and LDL receptor domain" American Journal of Physiology-Cell Physiology, vol. 293, No. 1, pp. C95-C105.

Agarwal, et al: "Site-Specific Antibody-Drug Conjugates: The Nexus of Bioorthogonal Chemistry, Protein Engineering, and Drug Development", Bioconjugate Chemistry, 2015, vol. 26, No. 2, pp. 176-192.

McCombs, et al: "Antibody drug conjugates: design and selection of linker, payload and conjugation chemistry.", The AAPS Journal, 2015, vol. 17, pp. 339-351.

Yao, et al: "Methods to Design and Synthesize Antibody-Drug Conjugates (ADCs)", International Journal of Molecular Sciences, Feb. 2016, vol. 17, No. 2, 194.

\* cited by examiner

Mammary epithelial cells

Breast cancer cells

Red: F-actin
Green: Activated matriptase
Yellow: Merged images

*10 mg M69-DOX = 0.035 mg DOX

TARGETING TUMOR CELLS WITH CHEMOTHERAPEUTIC AGENTS CONJUGATED TO ANTI-MATRIPTASE ANTIBODIES BY IN VIVO CLEAVABLE LINKING MOIETIES

CROSS-REFERENCE TO RELATED APPLICATIONS

The present application a continuation of U.S. Nonprovisional patent application Ser. No. 16/085,848, filed Sep. 17, 2018, which is a National Stage Entry of PCT/US17/22993, filed Mar. 17, 2017, which in turn claims priority to U.S. Nonprovisional patent application Ser. No. 15/075,008, filed Mar. 18, 2016, now U.S. Pat. No. 9,849,192, issued on Dec. 26, 2017. All of the foregoing references are hereby incorporated by reference in their entirety.

FIELD OF THE INVENTION

The present invention relates to new immunoconjugates comprising an anticancer agent and a monoclonal antibody and use of such immunoconjugates for killing or inhibiting the growth of matriptase expressing cancer cells, including but not limited to hematological malignancies and epithelial cancers, such as those of multiple myeloma and breast cancers. Thus, the present invention also relates to new methods of treating matriptase-expressing cancers.

BACKGROUND OF THE INVENTION

Matriptase is a type II transmembrane serine protease expressed by cells of epithelial origin, including breast and prostate tumor cells. Matriptase is characterized by an N-terminal transmembrane domain and multiple extracellular domains, in addition to the conserved extracellular domain (Lin C. Y., et al., J. Biol. Chem., 1999, 274(26): 18237-18242). Matriptase is a zymogen that needs to be activated by proteolytic cleavage to become a two-chain active enzyme. Under normal physiological conditions, there is excessive amount of endogenous inhibitor called HGF activator inhibitor-I (HAI-1) that binds to matriptase, tightly regulating the protease activity (Lin, C. Y., et al., J. Biol, Chem., 1999, 274: 18231-18236; Oberst, M. D., et al., J. Biol. Chem., 2003, 278:26773-26779). Besides exerting an inhibitory function, HAI-1 also plays a critical role in activation, proper expression and intracellular trafficking of matriptase (Oberst, M. D., et al., J. Biol. Chem., 2003, 278: 26773-26779; Oberst, M. D., et al., Am. J. Physiol. Cell Physiol., 2005, 289:C462-C470).

Matriptase is known to proteolytically activate the hepatocyte growth factor (HGF) and the urokinase plasminogen activator (uPA) and protease-activated receptor in vitro (Lee, S. L., et al., J. Biol. Chem., 2000, 275:36720-36725; Suzuki, M., et al., J. Biol. Chem., 2004, 279:14899-14908). Both HGF and uPA have been implicated for their roles in cellular invasion and metastasis and in cellular motility (Trusolino, L. and Comoglio, P. M., Nat. Rev. Cancer, 2002, 2:289-300; Sidenius, N. and Blasi, F., Cancer Metastasis Rev., 2003, 22:205-222). The cognate receptor for HGF is Met, a receptor tyrosine kinase. Upon the binding of HGF, Met can trigger multiple signaling pathways, including Ras-MAPK, PI3K, Src and Stat3, which eventually leads to invasive growth. High levels of Met combined with overexpression of matriptase are associated with a poor outcome for patients with breast cancer.

Studies of matriptase levels in several solid epithelial-derived tumors including breast, prostate and ovarian carcinomas have been performed in the past few years (for a review, see Uhland, K., Cell. Mol. Life Sci., 2007, 63(24): 2968-78). A tissue microarray from patients with breast carcinoma showed that high-level expression of Met, matriptase and HAI-1 are associated with poor patient outcome (Kang, J. Y., et al., Cancer Res., 2003, 63: 1 101-1105). In prostate tumors, increased levels of matriptase with decreased expression of HAI-1 were associated with increasing tumor grade (Saleem, M., et al., Cancer Epidemiol. Biomarkers Prev., 2006: 15, 217-227). Overexpression of matriptase was also found in 82% of stage III and in 55% stage III/VI of patients with ovarian cancer.

Given the significant roles of matriptase in tumor initiation, progression and metastases, several inhibitors for this protease have been investigated in animal models for their anticancer activity. Reduced tumor growth and metastasis formation by matriptase inhibitor, ecotin, has been shown in a PC-3 prostate carcinoma xenograft model (Takeuchi, N., et al., Proc. Natl. Acad. Sci. USA, 1999, 96, 11054-11061). CVS-3983, another matriptase inhibitor, also reduced tumor size in a mouse model of androgen-independent prostate cancer (Galkin, A. V., et al., Prostate, 2004, 61, 228-235).

Monomethyl auristatin E ("MMAE") is an FDA-approved synthetic antineoplastic agent that has shown promising use in chemotherapy based treatments. MMAE is a potent antimitotic compound but it exhibits high levels of cytotoxicity when administered alone, limiting its clinical value as a stand-alone compound. Monomethyl auristatin F ("MMAF"), also known as desmethyl-auristatin F, is an experimental synthetic anti-neoplastic agent that, like MMAE, is an antimitotic agent. Like MMAE, MMAF exhibits high levels of cytotoxicity when administered alone. Therefore, there is an urgent need for therapeutically effective antibody-based treatments that utilize MMAF and MMAE-bound immunoconjugates.

SUMMARY OF THE INVENTION

The present invention provides new therapeutic agents for the treatment of hematologic cancers, including acute lymphoblastic leukemia (ALL), acute myelogenous leukemia (AML), chronic lymphocytic leukemia (CLL), small lymphocytic lymphoma (SLL), chronic myelogenous leukemia (CML), acute monocytic leukemia (AMOL)), Hodgkin's lymphomas, Non-Hodgkin's lymphomas, Burkitt's lymphoma (BL), diffuse large B-cell lymphoma (DLBL), Mantle cell lymphoma (MCL), and multiple myeloma (MM), as well as new therapeutic agents for the treatment of various epithelial cancers, including prostate, breast, brain, kidney, lung, colon, bladder, skin, thyroid, and ovary tumors, and mesothelioma to meet the foregoing need.

Matriptase, a membrane-bound serine type II protease, is expressed in cell lines of multiple myeloma (MM) and other hematologic and epithelial cancer cells. The present invention provides an anti-matriptase antibody conjugated to a cytotoxic agent, for example, the auristatins MMAE and MMAF, for selectively targeting matriptase expressing cells. Antibodies conjugated with potent anticancer drugs to target matriptase-expressing cancer cells have various advantages. For example, the selective delivery of the chemotherapeutic agent to tumor cells overexpressing matriptase results in less toxicity toward the normal tissues. Moreover, since levels of matriptase mRNA have been found in tumors in other organs, including kidney, lung, colon, bladder, pancreas, prostate, skin, breast, thyroid and ovary, these immunoconjugates are useful for treating these cancers.

In one embodiment, the present invention provides an immunoconjugate of an anti-matriptase antibody and a cytotoxic agent. In some embodiments, the cytotoxic agent is selected from doxorubicin (DOX), auristatin, including monomethyl auristatin E (MMAE), monomethyl auristatin F (MMAF), calicheamicin, and ricin. In some embodiments, the cytotoxic agent is MMAE. In some embodiments, the cytotoxic agent is MMAF. In some embodiments the cytotoxic agent is covalently linked to the anti-matriptase antibody. In some embodiments the anti-matriptase antibody is M69. Therefore in some embodiments the immunoconjugate is MMAE covalently linked to M69. In other embodiments the immunoconjugate is MMAF covalently linked to M69.

In one embodiment, the present invention also provides for linkers for use in immunoconjugates. In some embodiments, the linkers comprise cleavable linking moieties. In some embodiments, the cleavable linking moieties comprise Val-Cit moieties or Phy-Lys moieties, cleavable by Capthesin B. In some embodiments, the linkers are conjugated directly to a surface of an antibody. In some embodiments, the linkers are covalently to a lysine side chain. In some embodiments, the linkers comprise a first linking component and a second linking component. In some embodiments, the first linking component is bound to the second linking component through a triazole moiety. In some embodiments, the first linking component is bound to a surface of an antibody. In some embodiments, the second linking component comprises a cleavable linking moiety. In some embodiments, the second linking component comprises a therapeutic agent. In some embodiments, the linker is PEG-based. In some embodiments, the first linking component is PEG-based. In some embodiments, the second linking component is PEG-based. In some embodiments, the antibody comprises an anti-matriptase antibody. In some embodiments, the anti-matrtiptase antibody comprises M69. In some embodiments, the therapeutic agent comprises a cytotoxic agent. In some embodiments, the cytotoxic agent is selected from doxorubicin (DOX), auristatin, including monomethyl auristatin E (MMAE), monomethyl auristatin F (MMAF), calicheamicin, and ricin. In some embodiments, the cytotoxic agent is MMAE. In some embodiments, the cytotoxic agent is MMAF.

Further, it has been discovered in accordance with the present invention that thalidomide, an immunomodulatory agent, markedly induces activation of matriptase in myeloma cells. Thus, the present invention provides for administration of immunoconjugates targeting active matriptase in combination with administration of immunomodulatory agents, including but not limited to thalidomide and its analogs, for the treatment of MM and other cancers. Thalidomide analogs are known in the art and include, for example, lenalidomide, CC-3052, CC-4047, CC-5103, IMiD3, EM12, and ENMD0995.

Thus, in one aspect the present invention provides a method of treating a hematological malignancy, comprising administering to a subject in need of such a treatment a composition comprising a therapeutically effective amount of an anti-matriptase antibody. In some embodiments, the anti-matriptase antibody is M69.

In another aspect the present invention provides a method of treating a hematological malignancy by administering to a subject in need of such a treatment a therapeutically effective amount of a composition containing an anti-matriptase antibody in combination with a therapeutically effective amount of an immunomodulatory agent that activates matriptase. In some embodiments the anti-matriptase antibody is M69. In some embodiments, the immunomodulatory agent is thalidomide or its analogs.

In another aspect the present invention provides a method of treating a malignancy in which malignant cells express matriptase by administering to a subject in need of such a treatment a therapeutically effective amount of a composition containing an immunoconjugate between an anti-matriptase antibody and a cytotoxic agent. In some embodiments the cytotoxic agent is selected from doxorubicin (DOX), auristatin, including monomethyl auristatin E (MMAE), monomethyl auristatin F (MMAF), and auristatin PE, calicheamicin, and ricin. In some embodiments, the cytotoxic agent is MMAE. In some embodiments, the cytotoxic agent is MMAF. In some embodiments the cytotoxic agent is covalently linked to the anti-matriptase antibody. In some embodiments the anti-matriptase antibody is M69. Therefore in some embodiments the immunoconjugate is MMAE covalently linked to M69. In other embodiments the immunoconjugate is MMAF covalently linked to M69.

In another aspect the present invention provides a method of treating a malignancy in which malignant cells express matriptase by administering to a subject in need of such a treatment a therapeutically effective amount of a composition containing an immunoconjugate between an anti-matriptase antibody and a cytotoxic agent in combination with a therapeutically effective amount of an immunomodulatory agent that activates matriptase. In some embodiments the cytotoxic agent is selected from doxorubicin (DOX), auristatin, including monomethyl auristatin E (MMAE), monomethyl auristatin F (MMAF), and auristatin PE, calicheamicin, and ricin. In some embodiments, the cytotoxic agent is MMAE. In some embodiments, the cytotoxic agent is MMAF In some embodiments the cytotoxic agent is covalently linked to the anti-matriptase antibody. In some embodiments the anti-matriptase antibody is M69. Therefore in some embodiments the immunoconjugate is MMAE covalently linked to M69. In other embodiments the immunoconjugate is MMAF covalently linked to M69. In some embodiments, the immunomodulatory agent is thalidomide or its analogs. Therefore, in some embodiments, the method comprises administration of a therapeutically effective amount of M69-MMAE immunoconjugates in combination with thalidomide or a thalidomide analog. In other embodiments, the method comprises administration of a therapeutically effective amount of M69-MMAF immunoconjugates in combination with thalidomide or a thalidomide analog. In other embodiments, the method comprises administration of a therapeutically effective amount of M69-auristatin PE immunoconjugates in combination with thalidomide or a thalidomide analog.

In another aspect the present invention provides an immunoconjugate selectively targeting cancer cells that express matriptase, comprising an anti-matriptase antibody and a cytotoxic agent.

In another aspect the present invention provides a composition containing an immunoconjugate selectively targeting cancer cells that express matriptase according to any of the embodiments described above.

In another aspect the present invention provides a method of diagnosing a hematological malignancy by contacting a test sample containing hematological cells from a mammal with an anti-matriptase antibody and detecting the formation of a complex between the antibody and matriptase, wherein formation of a complex is indicative of a malignancy.

In another aspect the present invention provides a method of inhibiting the growth of a hematopoietic cell that expresses matriptase by treating the hematopoietic cell with an anti-matriptase antibody or an immunoconjugate according to any of the embodiments described above.

In another aspect the present invention provides an assay kit for detecting expression of matriptase in mammalian tissues or cells, containing an immunoconjugate according to any of the embodiments described above.

In another aspect the present invention provides a kit for treatment of a malignancy in which malignant cells express matriptase, the kit comprising an immunoconjugate according to any of the embodiments described above.

In another aspect the present invention provides use of an immunoconjugate according to any of the embodiments described above for treatment of a malignancy in which malignant cells express matriptase.

In another aspect the present invention provides use of an immunoconjugate according to any of the embodiments described above for manufacture of a medicament for treatment of a malignancy in which malignant cells express matriptase.

These and other aspects of the present invention will be better appreciated by reference to the following drawings and detailed description.

DETAILED DESCRIPTION OF THE INVENTION

Figure 1A:
FIGS. 1A-D represent Western analyses of matriptase and HAI-1 in human lymphoma and myeloma cells. The cell lines in panel (A) include Hs 445 (lane 2), HuT 78 (lane 3), Farage (lane 4), Raji (lane 5), Daudi (lane 6), Namalwa (lane 7), Ramos (lane 8), ST486 (lane 9), SU-DHL-4 (lane 10), SU-DHL-6 (lane 11), OCI-LY-3 (lane 12), RPMI-8226 (lane 13). The cell lines in panel (B) include HL-60 (lane 2), Reh (lane 3), Jurkat (lane 4), SUP-T1 (lane 5), CCRF-CEM (lane 6), CCRF-HSB-2 (lane 7), MOLT-3 (lane 8), MOLT-4 (lane 9), CCRF-SB (lane 10), RS4-11 (lane 11), THP-1 (lane 12), U937 (lane 13). Panel (C) shows the assessment of levels of matriptase in three MM cell lines as indicated. GAPDH served as an internal control. Panel (D) shows the tissue sections of paraffin-embedded multiple myeloma stained with the matriptase mAb M24, the HAI-1mAb M19, and the activated matriptase M69, respectively as indicated.
Figure 1B:

While matriptase is mainly produced by normal epithelial and a variety of epithelial-derived carcinoma cells, it has been discovered in accordance with the present invention that this membrane-bound protease is also present in various cells of hematological malignancies. The present invention provides methods of treating hematological malignancies by administering antibodies to matriptase. The invention further provides immunoconjugates of an anti-matriptase antibody and a cytotoxic agent, and methods of using the immunoconjugates for treatment of malignancies in which cells express matriptase. In one preferred embodiment of this invention, an auristatin, e.g. MMAE, MMAF, or auristatin PE is conjugated with a monoclonal antibody to matriptase for targeting myeloma cells. In some embodiments, the antibody is M69. Thus, in some embodiments, the immunoconjugate is M69-auristatin, e.g. M69-MMAE, M69-MMAF, and/or M69-auristatin PE.

Thus, in a first aspect the present invention provides a method of treating a hematological malignancy by administering to a subject in need of such a treatment a composition containing a therapeutically effective amount of an anti-matriptase antibody.

In one embodiment of this aspect, the present invention provides a method of treating a hematological malignancy, wherein the hematological malignancy is a cancer comprising cells that express matriptase.

In another embodiment of this aspect, the present invention provides a method of treating a hematological malignancy, wherein the hematological malignancy is selected from leukemias, lymphomas, and myelomas.

In another embodiment of this aspect, the present invention provides a method of treating a hematological malignancy, wherein the hematological malignancy is selected from acute lymphoblastic leukemia (ALL), acute myelogenous leukemia (AML), chronic lymphocytic leukemia (CLL), small lymphocytic lymphoma (SLL), chronic myelogenous leukemia (CML), acute monocytic leukemia (AMOL), Hodgkin's lymphomas, Non-Hodgkin's lymphomas, Burkitt's lymphoma (BL), diffuse large B-cell lymphoma (DLBL), Mantle cell lymphoma (MCL), and multiple myeloma.

In another embodiment of this aspect, the present invention provides a method of treating a hematological malignancy, wherein the hematological malignancy is multiple myeloma.

In another embodiment of this aspect, the present invention provides a method of treating a hematological malignancy, wherein the hematological malignancy is a cancer in which the malignant cells express matriptase.

In another embodiment of this aspect, the present invention provides a method of treating a hematological malignancy, wherein the anti-matriptase antibody is a monoclonal antibody (mAb). In some embodiments, the monoclonal antibody is M69. In further embodiments, the anti-matriptase antibody is covalently linked to a cytotoxic compound. In yet further embodiments, a cytotoxic compound is auristatin, including MMAE, MMAF, and/or auristatin PE. Thus, in some embodiments, the present invention provides a method of treating a hematological malignancy by administering a therapeutically effective amount of an anti-matriptase antibody conjugated to MMAE, MMAF, and/or auristatin PE, and in further embodiments the anti-matriptase antibody is M69.

In another embodiment of this aspect, the present invention provides a method of treating a hematological malignancy, wherein the anti-matriptase antibody is selected from chimeric antibodies, humanized antibodies, and human antibodies.

In another embodiment of this aspect, the present invention provides a method of treating a hematological malignancy, wherein the composition further includes a pharmaceutically acceptable carrier.

In a second aspect the present invention provides a method of treating a hematological malignancy by administering to a subject in need of such a treatment a therapeutically effective amount of a composition containing an anti-matriptase antibody in combination with a therapeutically effective amount of an immunomodulatory agent that activates matriptase. In some embodiments, the immunomodulatory agent is thalidomide or a thalidomide analog.

In one embodiment of this aspect, the present invention provides a method of treating a hematological malignancy, wherein the malignancy is multiple myeloma.

In another embodiment of this aspect, the present invention provides a method of treating a hematological malignancy, wherein the anti-matriptase antibody is an antibody specific for activated matriptase.

In another embodiment of this aspect, the present invention provides a method of treating a hematological malignancy, wherein the anti-matriptase antibody is a mAb M69.

In another embodiment of this aspect, the present invention provides a method of treating a hematological malignancy, wherein the anti-matriptase antibody is an antigen-binding fragment.

In another embodiment of this aspect, the present invention provides a method of treating a hematological malignancy, wherein the anti-matriptase antibody is selected from the group consisting of chimeric antibodies, humanized antibodies, and human antibodies.

In another embodiment of this aspect, the present invention provides a method of treating a hematological malignancy, wherein the anti-matriptase antibody is a monoclonal antibody, and the immunomodulatory agent is thalidomide or a thalidomide analog.

In another embodiment of this aspect, the present invention provides a method of treating a hematological malignancy, wherein the immunomodulatory agent is administered to the subject for a sufficient amount of time so that matriptase is activated prior to administration of the composition comprising the anti-matriptase antibody.

In another embodiment of this aspect, the present invention provides a method of treating a hematological malignancy, wherein the composition further comprises a pharmaceutically acceptable carrier.

In a third aspect the present invention provides a method of treating a malignancy comprising cells that express matriptase, the method comprising administering to a subject in need of such a treatment a therapeutically effective amount of a composition comprising an immunoconjugate between an anti-matriptase antibody and a cytotoxic agent.

In one embodiment of this aspect, the present invention provides a method of treating a malignancy comprising cells that express matriptase, wherein the hematological malignancy is a cancer comprising cells that express matriptase.

In another embodiment of this aspect, the present invention provides a method of treating a malignancy comprising cells that express matriptase, wherein the malignancy is a cancer.

In another embodiment of this aspect, the present invention provides a method of treating a malignancy comprising cells that express matriptase, wherein the malignancy is a matriptase-positive malignant B cell lymphoma or an epithelial carcinoma.

In another embodiment of this aspect, the present invention provides a method of treating a malignancy comprising cells that express matriptase, wherein the malignancy is a matriptase-positive malignant B cell lymphoma selected from the group consisting of Mantle cell lymphoma (MCL), Burkitt's lymphoma (BL), and diffuse large B-cell lymphoma (DLBL).

In another embodiment of this aspect, the present invention provides a method of treating a malignancy comprising cells that express matriptase, wherein the malignancy is an epithelial carcinoma selected from the group consisting of prostate, breast, brain, kidney, lung, colon, bladder, and ovary as well as other tumor types, including thyroid tumor, skin tumor, and mesothelioma.

In another embodiment of this aspect, the present invention provides a method of treating a malignancy comprising cells that express matriptase, wherein the malignancy is selected from the group consisting of acute lymphoblastic leukemia (ALL), acute myelogenous leukemia (AML), chronic lymphocytic leukemia (CLL), small lymphocytic lymphoma (SLL), chronic myelogenous leukemia (CML), acute monocytic leukemia (AMOL), Hodgkin's lymphomas, Non-Hodgkin's lymphomas, Mantle cell lymphoma (MCL) and multiple myeloma.

In another embodiment of this aspect, the present invention provides a method of treating a malignancy comprising cells that express matriptase, wherein the malignancy is multiple myeloma.

In another embodiment of this aspect, the present invention provides a method of treating a malignancy comprising cells that express matriptase, wherein the anti-matriptase antibody is a monoclonal antibody (mAb). In some embodiments, the monoclonal antibody is M69.

In another embodiment of this aspect, the present invention provides a method of treating a malignancy comprising cells that express matriptase, wherein the anti-matriptase antibody is an antigen-binding fragment. In some embodiments, the antigen-binding fragment is an antigen binding fragment of M69.

In another embodiment of this aspect, the present invention provides a method of treating a malignancy comprising cells that express matriptase, wherein the anti-matriptase antibody is selected from the group consisting of chimeric antibodies, humanized antibodies, and human antibodies.

In another embodiment of this aspect, the present invention provides a method of treating a malignancy comprising cells that express matriptase, wherein the cytotoxic agent is selected from toxins, antibiotics, and compounds comprising radioactive isotopes.

In another embodiment of this aspect, the present invention provides a method of treating a malignancy comprising cells that express matriptase, wherein the cytotoxic agent is selected from doxorubicin (DOX), auristatin, including MMAE, MMAF, and auristatin PE, calicheamicin, and ricin.

In another embodiment of this aspect, the present invention provides a method of treating a malignancy comprising cells that express matriptase, wherein the cytotoxic agent is doxorubicin (DOX).

In another embodiment of this aspect, the present invention provides a method of treating a malignancy in which the malignant cells express matriptase, wherein the cytotoxic agent is auristatin.

In another embodiment of this aspect, the present invention provides a method of treating a malignancy in which the malignant cells express matriptase, wherein the cytotoxic agent is MMAE.

In another embodiment of this aspect, the present invention provides a method of treating a malignancy in which the malignant cells express matriptase, wherein the cytotoxic agent is MMAF.

In another embodiment of this aspect, the present invention provides a method of treating a malignancy in which the malignant cells express matriptase, wherein the cytotoxic agent is auristatin PE.

In another embodiment of this aspect, the present invention provides a method of treating a malignancy in which the malignant cells express matriptase, wherein the malignancy is a cancer refractory to the treatment of doxorubicin.

In another embodiment of this aspect, the present invention provides a method of treating a malignancy in which the malignant cells express matriptase, wherein the malignancy is a cancer refractory to the treatment of auristatin.

In another embodiment of this aspect, the present invention provides a method of treating a malignancy in which the malignant cells express matriptase, wherein the malignancy is a cancer refractory to the treatment of MMAE.

In another embodiment of this aspect, the present invention provides a method of treating a malignancy in which the malignant cells express matriptase, wherein the malignancy is a cancer refractory to the treatment of MMAF.

In another embodiment of this aspect, the present invention provides a method of treating a malignancy in which the malignant cells express matriptase, wherein the malignancy is a cancer refractory to the treatment of auristatin PE.

In another embodiment of this aspect, the present invention provides a method of treating a malignancy in which the malignant cells express matriptase, wherein the immunoconjugate is M24-DOX or M69-DOX.

In another embodiment of this aspect, the present invention provides a method of treating a malignancy in which the malignant cells express matriptase, wherein the immunoconjugate is M24-auristatin or M69-auristatin.

In another embodiment of this aspect, the present invention provides a method of treating a malignancy in which the malignant cells express matriptase, wherein the immunoconjugate is M24-MMAE or M69-MMAE.

In another embodiment of this aspect, the present invention provides a method of treating a malignancy in which the malignant cells express matriptase, wherein the immunoconjugate is M24-MMAF or M69-MMAF.

In another embodiment of this aspect, the present invention provides a method of treating a malignancy in which the malignant cells express matriptase, wherein the immunoconjugate is M24-auristatin PE or M69-auristatin PE.

In another embodiment of this aspect, the present invention provides a method of treating a malignancy in which the malignant cells express matriptase, wherein the cytotoxic agent is coupled to the anti-matriptase antibody through a covalent bond.

In another embodiment of this aspect, the present invention provides a method of treating a malignancy in which the malignant cells express matriptase, wherein the subject is a mammalian patient.

In another embodiment of this aspect, the present invention provides a method of treating a malignancy in which the malignant cells express matriptase, wherein the subject is a human.

In another embodiment of this aspect, the present invention provides a method of treating a malignancy in which the malignant cells express matriptase, wherein the composition further comprises a pharmaceutically acceptable carrier.

In a fourth aspect the present invention provides a method of treating a malignancy in which the malignant cells express matriptase, the method comprising administering to a subject in need of such a treatment a therapeutically effective amount of a composition comprising an immunoconjugate between an anti-matriptase antibody and a cytotoxic agent in combination with a therapeutically effective amount of an immunomodulatory agent that activates matriptase.

In one embodiment of this aspect, the present invention provides a method of treating a malignancy in which the malignant cells express matriptase, wherein the malignancy is multiple myeloma.

In another embodiment of this aspect, the present invention provides a method of treating a malignancy in which the malignant cells express matriptase, wherein the anti-matriptase antibody is an antibody specific for activated matriptase.

In another embodiment of this aspect, the present invention provides a method of treating a malignancy in which the malignant cells express matriptase, wherein the anti-matriptase antibody is a monoclonal antibody (mAb). In some embodiments, the monoclonal antibody is M69.

In another embodiment of this aspect, the present invention provides a method of treating a malignancy in which the malignant cells express matriptase, wherein the anti-matriptase antibody is an antigen-binding fragment. In some embodiments, the antigen-binding fragment is an antigen binding fragment of M69.

In another embodiment of this aspect, the present invention provides a method of treating a malignancy in which the malignant cells express matriptase, wherein the anti-matriptase antibody is selected from the group consisting of chimeric antibodies, humanized antibodies, and human antibodies.

In another embodiment of this aspect, the present invention provides a method of treating a malignancy in which the malignant cells express matriptase, wherein the anti-matriptase antibody is mAb M69, and the cytotoxic agent is doxorubicin (DOX).

In another embodiment of this aspect, the present invention provides a method of treating a malignancy in which the malignant cells express matriptase, wherein the anti-matriptase antibody is mAb M69, and the cytotoxic agent is auristatin.

In another embodiment of this aspect, the present invention provides a method of treating a malignancy in which the malignant cells express matriptase, wherein the anti-matriptase antibody is mAb M69, and the cytotoxic agent is MMAE.

In another embodiment of this aspect, the present invention provides a method of treating a malignancy in which the malignant cells express matriptase, wherein the anti-matriptase antibody is mAb M69, and the cytotoxic agent is MMAF.

In another embodiment of this aspect, the present invention provides a method of treating a malignancy in which the malignant cells express matriptase, wherein the anti-matriptase antibody is mAb M69, and the cytotoxic agent is auristatin PE.

In another embodiment of this aspect, the present invention provides a method of treating a malignancy in which the malignant cells express matriptase, wherein the immunomodulatory agent is thalidomide or a thalidomide analog.

In another embodiment of this aspect, the present invention provides a method of treating a malignancy in which the malignant cells express matriptase, wherein the immunomodulatory agent is administered to the subject for a sufficient amount of time so that matriptase is activated prior to administration of the composition comprising the immunoconjugate.

In another embodiment of this aspect, the present invention provides a method of treating a hematological malignancy, wherein: (a) the malignancy is multiple myeloma; (b) the immunoconjugate comprises an anti-matriptase antibody and DOX; and (c) the immunomodulatory agent is thalidomide or a thalidomide analog.

In another embodiment of this aspect, the present invention provides a method of treating a hematological malignancy, wherein (a) the immunoconjugate comprises an anti-matriptase antibody and auristatin; and (b) the immunomodulatory agent is thalidomide or a thalidomide analog.

In another embodiment of this aspect, the present invention provides a method of treating a hematological malignancy, wherein (a) the immunoconjugate comprises an anti-matriptase antibody and MMAE; and (b) the immunomodulatory agent is thalidomide or a thalidomide analog.

In another embodiment of this aspect, the present invention provides a method of treating a hematological malignancy, wherein (a) the immunoconjugate comprises an anti-matriptase antibody and MMAF; and (b) the immunomodulatory agent is thalidomide or a thalidomide analog.

In another embodiment of this aspect, the present invention provides a method of treating a hematological malignancy, wherein (a) the immunoconjugate comprises an anti-matriptase antibody and auristatin PE; and (b) the immunomodulatory agent is thalidomide or a thalidomide analog.

In a fifth aspect the present invention provides an immunoconjugate selectively targeting cancer cells that express matriptase, comprising an anti-matriptase antibody and a cytotoxic agent.

In one embodiment of this aspect, the present invention provides an immunoconjugate selectively targeting cancer cells that express matriptase, wherein the anti-matriptase antibody recognizes an antigen expressed on the surface of the cancer cells.

In another embodiment of this aspect, the present invention provides an immunoconjugate selectively targeting cancer cells that express matriptase, wherein the anti-matriptase antibody is a monoclonal antibody (mAb). In some embodiments, the monoclonal antibody is M69.

In another embodiment of this aspect, the present invention provides an immunoconjugate selectively targeting cancer cells that express matriptase, wherein the anti-matriptase antibody is an antigen-binding fragment. In some embodiments, the antigen-binding fragment is an antigen binding fragment of M69.

In another embodiment of this aspect, the present invention provides an immunoconjugate selectively targeting cancer cells that express matriptase, wherein the anti-matriptase antibody is selected from the group consisting of chimeric antibodies, humanized antibodies, and human antibodies.

In another embodiment of this aspect, the present invention provides an immunoconjugate selectively targeting cancer cells that express matriptase, wherein the anti-matriptase antibody is a monoclonal antibody, and the cytotoxic agent is selected from the group consisting of doxorubicin (DOX), auristatin, including MMAE, MMAF, and auristatin PE, calicheamicin, and ricin.

In another embodiment of this aspect, the present invention provides an immunoconjugate selectively targeting cancer cells that express matriptase, wherein the conjugate is formed through a covalent bond between the anti-matriptase antibody and the DOX moiety.

In another embodiment of this aspect, the present invention provides an immunoconjugate selectively targeting cancer cells that express matriptase, wherein one molecule of the anti-matriptase antibody is coupled with up to 15 molecules of DOX.

In another embodiment of this aspect, the present invention provides an immunoconjugate selectively targeting cancer cells that express matriptase, wherein one molecule of the anti-matriptase antibody is coupled with about 5-10 molecules of DOX.

In another embodiment of this aspect, the present invention provides an immunoconjugate selectively targeting cancer cells that express matriptase, wherein one molecule of the anti-matriptase antibody is coupled about 7 molecules of DOX.

In another embodiment of this aspect, the present invention provides an immunoconjugate selectively targeting cancer cells that express matriptase, wherein the conjugate is formed through a covalent bond between the anti-matriptase antibody and an auristatin moiety.

In another embodiment of this aspect, the present invention provides an immunoconjugate selectively targeting cancer cells that express matriptase, wherein one molecule of the anti-matriptase antibody is coupled with up to 10 molecules of auristatin, including MMAE, MMAF, and/or auristatin PE.

In another embodiment of this aspect, the present invention provides an immunoconjugate selectively targeting cancer cells that express matriptase, wherein one molecule of the anti-matriptase antibody is coupled with about 5-10 molecules of auristatin, including MMAE, MMAF, and/or auristatin PE.

In another embodiment of this aspect, the present invention provides an immunoconjugate selectively targeting cancer cells that express matriptase, wherein one molecule of the anti-matriptase antibody is coupled about 3-5 molecules of auristatin, including MMAE, MMAF, and/or auristatin PE.

In another embodiment of this aspect, the present invention provides an immunoconjugate selectively targeting cancer cells that express matriptase, wherein one molecule of the anti-matriptase antibody is coupled about 3 molecules of auristatin, including MMAE, MMAF, and/or auristatin PE.

In another embodiment of this aspect, the present invention provides an immunoconjugate selectively targeting cancer cells that express matriptase, wherein one molecule of the anti-matriptase antibody is coupled about 1-3 molecules of auristatin, including MMAE, MMAF, and/or auristatin PE.

In another embodiment of this aspect, the present invention provides an immunoconjugate selectively targeting cancer cells that express matriptase, the immunoconjugate having reduced or no cardiotoxicity in comparison with the cytotoxic agent when administered in the absence of the anti-matriptase antibody.

In another embodiment of this aspect, the present invention provides an immunoconjugate selectively targeting cancer cells that express matriptase, the immunoconjugate having minimized or no adverse effects on bone marrow-derived mesenchymal stromal cells which do not express matriptase.

In another aspect the present invention provides a composition comprising an immunoconjugate selectively targeting cancer cells that express matriptase according to any of the embodiments described above in the fifth aspect.

In one embodiment of this aspect, the present invention provides an immunoconjugate selectively targeting cancer cells that express matriptase, further comprising a pharmaceutically acceptable carrier.

In another aspect the present invention provides an immunoconjugate comprising a linker. In some embodiments, the antibody comprises an anti-matriptase antibody. In some embodiments, the anti-matriptase antibody comprises M69. In some embodiments, the immunoconjugate comprising a linker comprises a therapeutic agent. In some embodiments, the therapeutic agent is any therapeutic agent according to the present disclosure. In some embodiments, the therapeutic agent comprises auristatin. In some embodiments, the therapeutic agent comprises MMAE.

In some embodiments, the linker comprises a cleavable linking moiety. In some embodiments, the cleavable linking moiety comprises a Cit-Val linking moiety. In some embodiments, the cleavable linker comprises a Phe-Lys linking moiety. In some embodiments, the cleavable linking moiety is cleavable by Capthesin B.

In some embodiments, the linker is conjugated to a surface of an antibody. In some embodiments, the antibody comprises an anti-matriptase antibody. In some embodiments, the anti-matriptase antibody comprises M69. In some embodiments, the linker is covalently bound to an exposed amino acid residue. In some embodiments, the exposed amino acid residue comprises a cysteine. In further embodiments, the linker is covalently bound to the cysteine through sulfhydryl-maleimide coupling. In some embodiments, the exposed amino acid residue comprises a lysine. In further embodiments, the linker is covalently bound to the lysine through an amide linkage formed by acylation.

In some embodiments, the linker comprises a first linking component and a second linking component. In some embodiments, the first linking component is conjugated to a surface of an antibody according to any aspect of the present disclosure. In some embodiments, the first linking component is linked to the second linking component. In some embodiments, the first linking component is linked to the second linking component through click chemistry. In some embodiments, the first linking component is linked to the second linking component through a triazole moiety. In some embodiments, the second linking component comprises a cleavable linking moiety according to any aspect of the present disclosure. In some embodiments, the second linking component comprises a therapeutic agent according to any aspect of the present disclosure. In some embodiments, the therapeutic agent comprises a cytotoxic agent. In some embodiments, the cytotoxic agent is selected from doxorubicin (DOX), auristatin, including monomethyl auristatin E (MMAE), monomethyl auristatin F (MMAF), calicheamicin, and ricin. In some embodiments, the cytotoxic agent is MMAE. In some embodiments, the cytotoxic agent is MMAF.

In some embodiments, the linker is PEG-containing. In some embodiments, a first linking component is PEG-containing. In some embodiments, a second linking component is PEG-containing. In some embodiments, a first linking component and a second linking component are PEG-containing.

In another aspect, the present invention provides for an immunoconjugate comprising an anti-matriptase antibody covalently bound to a first linking component through a lysine side chain, the first linking component being PEG-containing, the first linking component bound to a second linking component through a triazole moiety, the second linking component having a cleavable linking moiety and a therapeutic agent, and the second linking component being PEG-containing. In some embodiments, the anti-matriptase antibody comprises M69. In some embodiments, the first linking component contains between 1 and 10 PEG units. In some embodiments, the second linking component contains between 1 and 10 PEG units. In some embodiments, the cleavable linking moiety comprises a Val-Cit moiety. In some embodiments, the cleavable linking moiety comprises a Phe-Lys moiety. In some embodiments, the therapeutic agent comprises a cytotoxic agent. In some embodiments, the cytotoxic agent is selected from doxorubicin (DOX), auristatin, including monomethyl auristatin E (MMAE), monomethyl auristatin F (MMAF), calicheamicin, and ricin. In some embodiments, the cytotoxic agent is MMAE. In some embodiments, the cytotoxic agent is MMAF.

In another aspect the present invention provides a method of diagnosing a hematological malignancy comprising contacting a test sample containing hematological cells from a mammal with an anti-matriptase antibody and detecting the formation of a complex between the antibody and matriptase, wherein formation of a complex is indicative of a malignancy.

In another aspect the present invention provides a method of inhibiting the growth of a hematopoietic cell that expresses matriptase, the method comprising treating the hematopoietic cell with an anti-matriptase antibody or an immunoconjugate according to any of the embodiments described above.

In another aspect the present invention provides an assay kit for detecting expression of matriptase in mammalian tissues or cells, comprising an immunoconjugate according to any of the embodiments described above.

In another aspect the present invention provides a kit for treatment of a malignancy comprising cells that express matriptase, the kit comprising an immunoconjugate according to any of the embodiments described above.

In another aspect the present invention provides use of an immunoconjugate according to any of the embodiments described above for treatment of a malignancy comprising cells that express matriptase.

In another aspect the present invention provides use of an immunoconjugate according to any of the embodiments described above for manufacture of a medicament for treatment of a malignancy comprising cells that express matriptase.

Definitions

As used herein, the term "biological sample" refers to a specimen comprising body fluids, cells or tissue from a subject, preferably a human subject. The sample can also be body fluid that has come into contact, either naturally or by artificial methods (e.g. surgical means), with a malignant cell or cells of a pre-malignant lesion.

As used herein, the term "expression of matriptase," or the like, refers to any biological sample comprising one or more cells which express a form or forms of matriptase.

As used herein, the term "subject" refers to an animal, preferably mammalian, and most preferably human.

As used herein, the term "antibody" refers to complete, intact antibodies, and Fab fragments and F(ab), fragments thereof. Complete, intact antibodies include monoclonal antibodies such as murine monoclonal antibodies (mAb), chimeric antibodies, humanized antibodies, and human antibodies.

An "antibody fragment" can be prepared by known methods, for example, as disclosed by Goldenberg, U.S. Pat. Nos. 4,036,945 and 4,331,647 and references contained therein. Another form of an antibody fragment is a peptide coding for a single complementarity-determining region (CDR). A CDR is a segment of the variable region of an antibody that is complementary in structure to the epitope to which the antibody binds and is more variable than the rest of the variable region. CDR peptides can be obtained by constructing genes encoding the CDR of an antibody of interest. Such genes are prepared, for example, by using the polymerase chain reaction to synthesize the variable region from RNA of antibody-producing cells.

As used herein, the term "immunoconjugate" refers to a conjugate of an antibody component with a molecule or a therapeutic or diagnostic agent. The therapeutic or diagnostic agent can comprise a radioactive or non-radioactive label. The antibodies that used to prepare immunoconjugates include, but is not limited to, monoclonal antibodies, chimeric antibodies, humanized antibodies, and human antibodies. Here a preferred immunoconjugate is a conjugate between a matriptase monoclonal antibody and a cytotoxic agent, and a more preferred immunoconjugate is one comprising a matriptase monoclonal antibody and a FDA-approved anticancer agent, including but not limited to doxorubicin (DOX), auristatin, calicheamicin, or ricin.

As used herein, the term "cytotoxic agent" refers to a substance that inhibits or prevents the function of cells and/or causes destruction of cells. The term is intended to include chemotherapeutic agents, such as methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. The term also encompasses compounds comprising one or more radioactive isotopes (e.g., At211, I131, I125, Y90, Re186, Re188, Sm153, Bi212, P32, as well as radioactive isotopes of Lu).

As used herein, the term "doxorubicin" (or "DOX") refers to an anthracycline antibiotic with a systematic (IUPAC) chemical name of (8S,10S)-10-(4-amino-5-hydroxy-6-methyl-tetrahydro-2H-pyran-2-yloxy)-6,8,11-trihydroxy-8-(2-hydroxyacetyl)-1-methoxy-7,8,9,10-tetrahydrotetracene-5,12-dione.

As used herein, the term "auristatin" includes, but is not limited to, the antimitotic agents monomethyl auristatin E ("MMAE"). monomethyl auristatin F ("MMAF"), also known as desmethyl-auristatin F. and auristatin PE. MMAE has a systematic (IUPAC) chemical name of (S)—N-((3R, 4S,5S)-1-((S)-2-((1R,2R)-3-(((1S,2R)-1-hydroxy-1-phenyl-propan-2-yl)amino)-1-methoxy-2-methyl-3-oxopropyl)pyr-rolidin-1-yl)-3-methoxy-5-methyl-1-oxoheptan-4-yl)-N,3- dimethyl-2-((S)-3-methyl-2-(methylamino)butanamido) butanamide. MMAF has a systematic (IUPAC) chemical name of (S)-2-((2R,3R)-3-((S)-1-((3R,4S,5S)-4-((S)—N,3-dimethyl-2-((S)-3-methyl-2-(methylamino)butanamido)butanamido)-3-methoxy-5-methylheptanoyl)pyrrolidin-2-yl)-3-methoxy-2-methylpropanamido)-3-phenylpropanoic acid. Auristatin PE has a systematic (IUPAC) chemical name of 2-[[(2S)-2-(dimethylamino)-3-methylbutanoyl]amino]-N-[(3R,4S,5S)-3-methoxy-1-[(2S)-2-[(1R,2R)-1-methoxy-2-methyl-3-oxo-3-(2-phenylethylamino)propyl]pyrrolidin-1-yl]-5-methyl-1-oxoheptan-4-yl]-N,3-dimethylbutanamide.

As used herein, the term "carrier" refers to a molecule or higher-ordered structure that is capable of associating with a therapeutic or diagnostic agent to facilitate delivery of the agent to a targeted cell. Carriers may include molecules such as lipids or polymers, such as amphiphilic lipids or carbohydrates, or higher-ordered structures, such as micelles, liposomes, and nanoparticles.

The immunoconjugates or compositions disclosed herein can be formulated according to known methods and may include one or more pharmaceutically suitable excipients, one or more additional ingredients, or combinations thereof.

The immunoconjugates or compositions disclosed herein can be formulated for intravenous administration via, for example, bolus injection or continuous infusion. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The immunoconjugate or compositions may also be administered to a mammal subcutaneously or even by other parenteral routes. Moreover, the administration may be by continuous infusion or by single or multiple boluses. In general, the dosage of an administered immunoconjugate will vary depending upon such factors as the patient's age, weight, height, sex, general medical condition and previous medical history.

Additional pharmaceutical methods may be employed to control the duration of action of the therapeutic or diagnostic conjugate or naked antibody. Control release preparations can be prepared through the use of polymers to complex or adsorb the immunoconjugate or naked antibody.

An antibody preparation is said to be administered in a "therapeutically effective amount" if the amount administered is physiologically significant. An agent is physiologically significant if its presence results in a detectable change in the physiology of a recipient mammal, including a reduction in the number of cancer cells, a reduction in the size of a tumor, or an inhibition in the growth of a tumor. In particular, an antibody preparation is physiologically significant if its presence invokes an antitumor response or mitigates the signs and symptoms of an autoimmune disease state. A physiologically significant effect could also be the evocation of a humoral and/or cellular immune response in the recipient mammal It will be appreciated that actual preferred amounts of a pharmaceutical composition used in a given therapy will vary depending upon the particular form being utilized, the particular compositions formulated, the mode of application the particular site of administration, the patient's weight, general health, sex, etc., the particular indication being treated, etc. and other such factors that are recognized by those skilled in the art including the attendant physician or veterinarian. Optimal administration rates for a given protocol of administration can be readily determined by those skilled in the art using conventional dosage determination tests.

Preparation of Immunoconjugates

The immunoconjugates described herein can be prepared by known methods of linking antibodies with lipids, carbohydrates, protein, or other molecules. For example, the binding molecules described herein can be conjugated with one or more of the carriers described herein (e.g., lipids, polymers, liposomes, micelles, or nanoparticles) to form an immunoconjugate, and the immunoconjugate can incorporate a therapeutic or diagnostic agent either covalently, non-covalently, or otherwise. Further, any of the binding molecules described herein can be further conjugated with one or more therapeutic or diagnostic agents described herein, or additional carriers. Generally, one therapeutic or diagnostic agent may be attached to each binding molecule but more than one therapeutic agent or diagnostic agent can be attached to the same binding molecule. Further, the therapeutic agents do not need to be the same but can be different therapeutic agents.

For example, to synthesize an immunoconjugate of an antibody and DOX, DOX may be first reacted with succinimidyl 4-[N-maleimidomethyl]cyclohexane-1-carboxylate (SMCC), and the antibody against matriptase may be reacted with N-succinimidyl-3-(2-pyridyldithio)propionate (SPDP), followed by coupling of these two intermediates. Additional linkers that may be used to prepare immunoconjugates are discussed infra in the section titled "Linkers (Cleavable and Non-cleavable)".

Methods of Treatment

The present invention encompasses use of the matriptase antibodies or immunoconjugates or compositions comprising the matriptase antibodies or immunoconjugates as the primary composition for treatment of a malignancy comprising cells that express matriptase. The malignancy includes, but is not limited to, solid tumor, non-Hodgkin's lymphoma, Hodgkin's lymphoma, multiple myeloma, a B-cell malignancy and/or a T-cell malignancy. The solid tumor is selected from the group consisting of a melanoma, carcinoma and sarcoma and the carcinoma is selected from the group consisting of a renal carcinoma, lung carcinoma, intestinal carcinoma, stomach carcinoma and melanoma. The B-cell malignancy is selected from the group consisting of indolent forms of B-cell lymphomas, aggressive forms of B-cell lymphomas, chronic lymphatic leukemias, acute lymphatic leukemias, and multiple myeloma, B-cell disorders and other diseases. In particular, the compositions described herein are particularly useful for treatment of various auto-immune as well as indolent forms of B-cell lymphomas, aggressive forms of B-cell lymphomas, chronic lymphatic leukemias, acute lymphatic leukemias, multiple myeloma, and Waldenstrom's macroglobulinemia. The methods of treatment comprise administering to a mammal in need of such treatment a therapeutically effective amount of a composition comprising the antibody or immunoconjugate.

Antibodies

Antibodies against matriptase ("anti-matriptase antibodies") can be made by methods known in the art and disclosed, for example, by Lin C. Y., et al., J. Biol. Chem., 1999, 274 (26):18237-18242. Antibodies against matriptase include antibodies that are specific for latent matriptase, antibodies that are specific for activated matriptase, and antibodies that recognize both latent and activated matriptase.

The antibodies and immunogenic portions thereof of this invention are administered at a concentration that is therapeutically effective to prevent or treat any of the aforementioned disease states. To accomplish this goal, the antibodies may be formulated using a variety of acceptable excipients known in the art. Typically, the antibodies are preferably administered by injection, either intravenously or intraperitoneally. Methods to accomplish this administration are known to those of ordinary skill in the art. The compositions may also be topically or orally administered, or be capable of transmission across mucous membranes.

Before administration to patients, formulants may be added to the antibodies. A liquid formulation is preferred. For example, these formulants may include oils, polymers, vitamins, carbohydrates, amino acids, salts, buffers, albumin, surfactants, or bulking agents. Preferably carbohydrates include sugar or sugar alcohols, such as mono-, di- or polysaccharides, or water soluble glucans. The saccharides or glucans can include fructose, dextrose, lactose, glucose, mannose, sorbose, xylose, maltose, sucrose, dextran, pullulan, dextrain, alpha- and beta-cyclodextrin, soluble starch, hydroxyethyl starch and carboxymethylcellulose, or mixtures thereof.

Additionally, antibodies can be chemically modified by covalent conjugation to a polymer to increase their circulating half-life. Preferred polymers, and methods to attach them to peptides, are shown in U.S. Pat. Nos. 4,766,106; 4,179,337; 4,495,285; and 4,609,546. Preferred polymers are polyoxyethylated polyols and polyethylene glycol (PEG). Water soluble polyoxyethylated polyols are also useful in the present invention. They include polyoxyethylated sorbitol, polyoxyethylated glucose, polyoxyethylated glycerol (POG), etc.

The anti-matriptase antibodies of the present invention may comprise chimeric or humanized antibodies. Both chimeric and humanized antibodies comprise antibodies that are originally derived from non-human species which have been chemically modified to increase the similarity to antibody variants which are produced naturally in humans, and consequentially less immunogenic. Both chimeric and humanized antibodies are typically recombinantly produced and expressed in mammalian cell culture, e.g. through CHO cells. Such techniques are known to one of ordinary skill in the art. The primary difference between chimeric anti-matriptase antibodies and humanized anti-matriptase antibodies is that chimeric anti-matriptase antibodies typically comprise a substitution of the Fc region of the monoclonal antibody with a human Fc region, whereas humanized antibodies are identical to a human immunoglobulin (typically referred to as a human antibody "scaffold") except the complementarity determining regions (CDRs) are "swapped in" from the original mAb.

Another drug delivery system for increasing circulatory half-life is the liposome. Methods of preparing liposome delivery systems are discussed in Gabizon et al., Cancer Res. 42: 4734-9 (1982); Szoka et al., Annu. Rev. Biophys. Bioeng. 9: 467-508 (1980); Szoka et al., Meth. Enzymol. 149: 143-7 (1987); and Langne et al., Pol. J. Pharmacol. 51: 211-22 (1999). Other drug delivery systems are known in the art.

Linkers (Cleavable and Non-Cleavable)

The anti-matriptase antibodies of the present disclosure, e.g. M69, may be covalently linked to a therapeutic or diagnostic agent, e.g. DOX, auristatins, (including but not limited to MMAE/MMAF), thus forming an immunoconjugate. An overview of immunoconjugate linker-based technology is found in Jain N et al. Current ADC Linker Chemistry, Pharm Res. 2015 November; 32(11):3526-40, hereby incorporated by reference in its entirety. The covalent linkages in such immunoconjugates may comprise a cleavable linking moiety, for example, a Val-Cit linker, which is cleavable by Cathepsin B inside the lysosome. A commercially available Val-Cit linker was modified for use in Example 10 infra. Other cleavable linking moieties may comprise a Phe-Lys linker, which is also cleavable by Cathespin B. Some of the simplest cleavable linking moieties include disulfide (S—S) bridges, which are cleavable in a reductive (i.e. intracellular) environment. However, cleavable linking moieties such as Val-Cit linkers provide more specificity than, for example, disulfide bridges, which may be subject to indiscriminate cleavage, and thus present a superior option, although any such cleavable linking moiety is to be considered within the scope of the present invention. An overview of cleavable linking moieties which may be suitable for the present invention is provided in Leriche et al., Cleavable linkers in chemical biology Bioorg Med Chem. 2012 Jan. 15; 20(2):571-82, hereby incorporated by reference in its entirety. Alternatively, the linker may non-cleavable. Non-cleavable linkers are more diverse than cleavable linkers, and may comprise any linking moiety that is resistant to cleavage in an intracellular environment. For example, a specific non-cleavable linker which may be of interest comprises a SMCC linker, which is found in the FDA approved immunoconjugate trastuzumab emtansine (trade name Kadcyla), and is also explored in Example 2, infra, for preparation of M69-DOX immunoconjugates.

The linkers (and the therapeutic agents bound to said linkers) of the present disclosure may be directly conjugated to the antibody, i.e. covalently linked to the immunoglobulin. The covalent linkage may occur directly to one of the amino acids comprising the immunoglobulin backbone, ideally located within one of the constant domains, as opposed to within the variable domains. Such amino acids may be naturally occurring (e.g. a naturally occurring lysine or cysteine residue) or, the immunoglobulin may be artificially mutated (e.g. a non-naturally occurring lysine or cysteine residue) in order to provide an optimal binding site with minimal steric hindrance for the linker to bind to. Alternatively, the linker can be bound to a chemical moiety (e.g. bound to an N-glycan) found on post-translationally modified immunoglobulins.

The majority of immunoconjugates utilize direct attachment of the linker to a cysteine residue located in the antibody backbone. These linkers are known as "maleimide-type linkers" and utilize the reactivity of maleimide with sulfhydryl side chains found in cysteine (Cys). The two most common types of maleimide linkers include maleimidocaproyl (mc) and maleimidomethyl cyclohexane-1-carboxylate (mcc) linkers. A downside of maleimide linkers has been chemical instability in plasma, including a retro-Michael reaction which results in premature loss of the drug-linker from the immunoconjugate. A different type of direct conjugation, and one used in Example 10 infra, is direct conjugation to the s-amino side chain of lysine (Lys) side chain via acylation, creating an amide bond between the linker and the antibody in which the linker consists of an activated carboxyl group instead an azide functional group.

Figure 11:
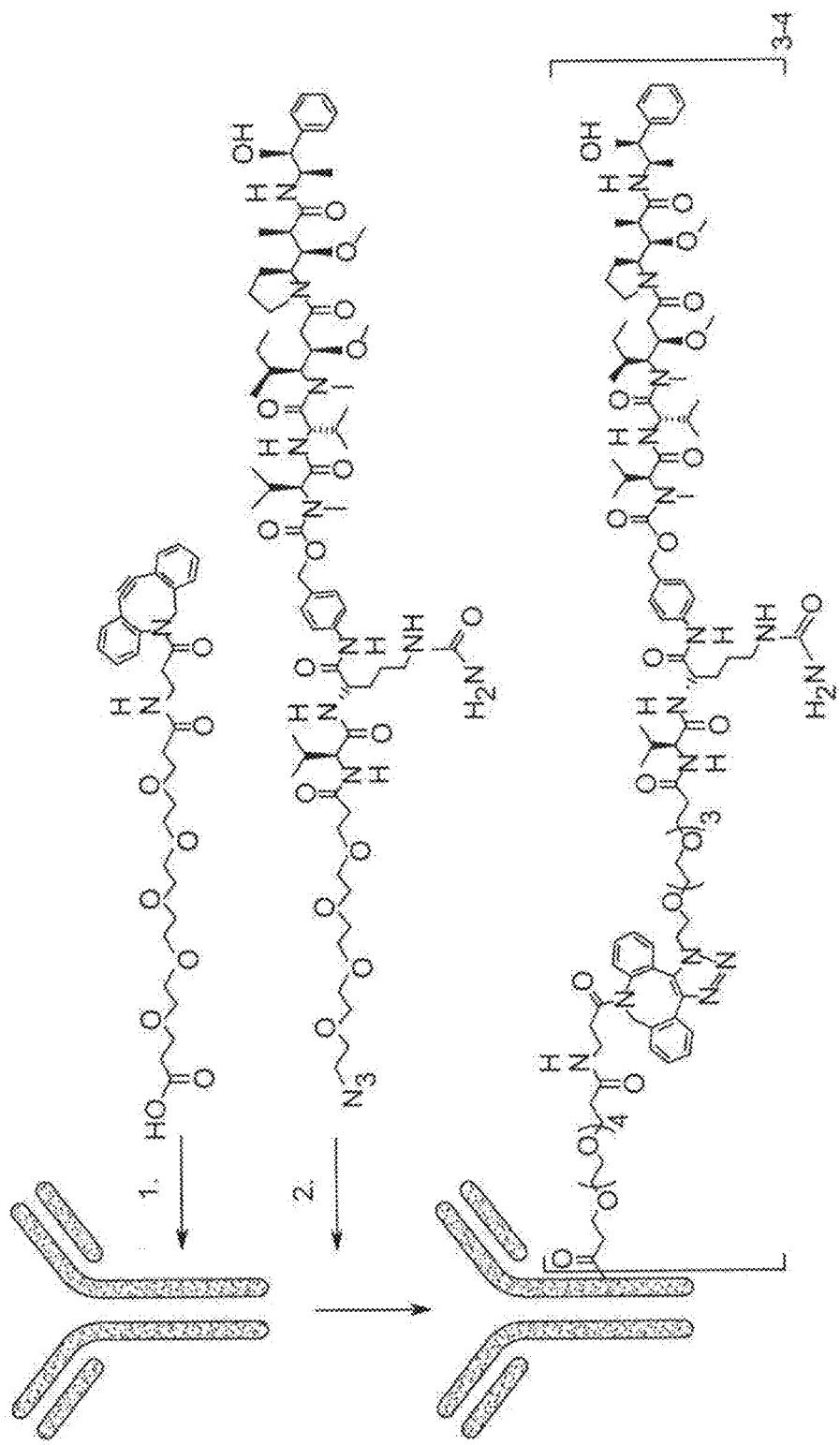
FIG. 11 illustrates the conjugation between MMAE and M69 utilizing lysine side chains with $PEG_5$-DBCO.
Figure 12:
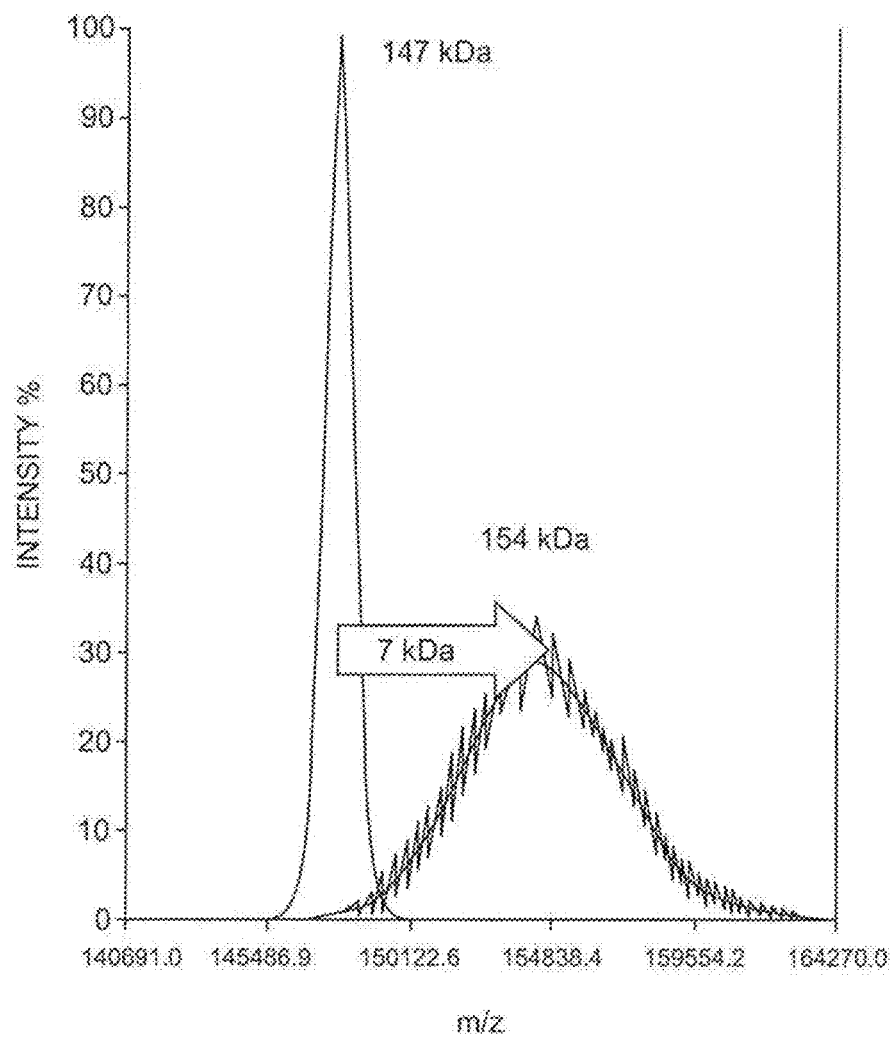
FIG. 12 illustrates an MALDI-TOF analysis of the immunoconjugate M69-MMAE after applying the chemical steps depicted in FIG. 11.

The linker and the therapeutic agent may be conjugated to the antibody using two-step conjugation technology as described herein. This two-step conjugation technology may utilize "click chemistry," especially copper-free click chemistry. Use of click chemistry in antibody conjugation may provide several unique benefits, for example, UV based detection of the forming click ring system for reaction monitoring and ADR determination. The linker may be initially comprised of two distinct linking components, for example (but not necessarily), one linking component containing an acylating agent (such as, for example, a carboxylic acid, acyl halide, or anhydride) that conjugates (i.e. acylates) to a lysine side chain located in the immunoglobulin backbone and further containing a strained alkyne (e.g. DBCO), and a second linking component containing an azide ($N_3$) group and the therapeutic agent, such that when the first component and the second component are brought within proximity to one another, the strained alkyne reacts with the azide group (forming a triazole moiety), linking the first linking component to the second linking component. Either the first linking moiety or the second linking moiety may contain the strained alkyne group and/or the azide group, and vice versa; i.e. the first linking moiety may comprise a strained alkyne and the second linking moiety an azide group, or the first linking moiety may comprise an azide group and the second linking moiety may comprise an a strained alkyne. Accordingly, when bound through "click chemistry" the linkers of the present disclosure may comprise a triazole moiety, e.g. a triazole moiety as formed between the reaction of DBCO with $N_3$ as illustrated in FIG. 11.

Thus in some embodiments, the overall structure of the immunoconjugate would comprise mAb-first linking component-second linking component-therapeutic agent, the first linking component being conjugated to the second linking component via a triazole moiety (formed by click chemistry), and the first linking component being conjugated to an amino acid residue (e.g. cysteine or preferably lysine as described herein) located in the immunoglobulin backbone. In such embodiments, incorporation of a cleavable linking moiety into either of the first and/or second linking components, e.g. a Val-Cit linker, is possible and is shown in FIG. 11. Ideally, the cleavable linking moiety would be located in the second linking component (i.e. the linking component containing the therapeutic agent, e.g. MMAE and/or MMAF).

The linkers in the immunoconjugates of the present disclosure may be PEG-based linkers. For example, and as shown in FIG. 11, in some embodiments both the first linking component and the second linking component (and thus the overall linker) contain poly(ethylene) glycol (PEG) repeats. PEG-based linkers may provide a distinct number of advantages over linkers not containing PEG. For example, PEG-based linkers may provide greater flexibility, so that, for example, in an instance where the linker is conjugated to an amino acid residue that is in close proximity to the antigen-binding domain (e.g. the hypervariable region), there would be a reduced chance that the linker/therapeutic agent would bind or interact with the surface elements of the antigen/receptor, thus making the overall immunoconjugate more therapeutically effective. Additionally, in such embodiments where linker is generated through click chemistry (e.g. using DBCO and $N_3$), while not wishing to be bound by theory, the use of PEG in the linking components may act as a spacer to prevent non-specific interactions (pi-pi interactions) between the tetracyclic ring structure found in the triazole moiety and any exposed aromatic side chains, especially tryptophan side chains. The PEG-based linkers of the present disclosure may comprise repeats of anywhere between 1-20 PEG units total, e.g. 1-10 PEG units per each of the first linking component and second linking component in such embodiments that utilize a first linking component and a second linking component. More typically, 3-7 PEG units per each of the first linking component and second linking components. By way of example, Example 10 infra shows an M69-MMAE immunoconjugate that contains 5 PEG units for the first linking component and 4 for the second linking component.

Auristatins, MMAE, MMAF

Auristatins, including MMAE, represent a class of very potent cytotoxic agents. Without wishing to be bound by theory, it is believed that auristatins like MMAE inhibit cell division by blocking the polymerization of tubulin, which is critical for proper cell division. Thus, compounds such as MMAE, MMAF, and auristatin PE are classified as "anti-mitotic agents" for inhibiting mitosis. The potency of such cytotoxic agents is significant. MMAE, for example, is 100 to 1000 times more potent than DOX, although DOX is suitable for use in this invention. Because of this potent toxicity, MMAE is not suitable for administration as a drug by itself. However, when coupled to an antibody such as matriptase antibodies, e.g. M69, the cytotoxic payload is capable of being directed to specific malignant cells.

As stated above, the antibodies and compositions of this invention are used preferably to treat human patients to prevent or treat any of the above-defined disease states. The preferred route of administration is parenteral. In parenteral administration, the compositions of this invention will be formulated in a unit dosage injectable form such as a solution, suspension or emulsion, in association with a pharmaceutically acceptable parenteral vehicle. Such vehicles are inherently nontoxic and non-therapeutic. Examples of such vehicles are saline, Ringer's solution, dextrose solution, and Hanks' solution. Non-aqueous vehicles such as fixed oils and ethyl oleate may also be used.

The anti-matriptase immunoconjugates disclosed herein, including mAb-auristatin and mAb-Dox conjugates represent examples for developing anticancer agents specifically targeting cancer cells. Anti-matriptase mAbs can be linked to other types of cytotoxic agent such as anti-tubulin compounds that would work better with certain types of tumors, or can be coupled to lyposomal or nanoparticles for targeted delivery of any types of agents, including peptides, shRNA/siRNA and very toxic compounds of little potential in cancer treatment due to severe side effects.

The following non-limiting examples further illustrate certain aspects of the invention.

EXAMPLES

Example 1

Expression of Matriptase in Multiple Myeloma and B-Cell Lymphoma Cells

A panel of 24 cell lines of human hematopoietic malignancies was analyzed by Western blotting for matriptase as well as its endogenous inhibitor HGF activator inhibitor-1 or HAI-1 (FIG. 1). Cell lysates were prepared from 24 hematopoietic cancer cells (lanes 2-14) and T-47D breast cancer cells (lane 1). Equal amounts of proteins were resolved by SDS-PAGE. Levels of matriptase and HAI-1 were assessed by immunoblot analyses using an anti-matriptase mAb and anti-HAI-1 mAb as indicated (FIGS. 1A and 1B).

Matriptase was expressed in the majority of the B-cell lymphomas as well as in multiple myeloma cells, indicating that the protease is an important marker for these cancers. In contrast, HAI-1 levels in lymphoma and myeloma appear to be much lower than those in carcinomas, and HAI-1 expression is often lost in highly aggressive lymphomas (Table 1).

To further verify the expression of matriptase in multiple myeloma cells, six cases of paraffin-embedded MM specimens were examined. Matriptase was positive in four cases, among which two were HAI-1 positive and the other two were negative (FIG. 1D).

Figure 1C:
Figure 1C:
Figure 1C:
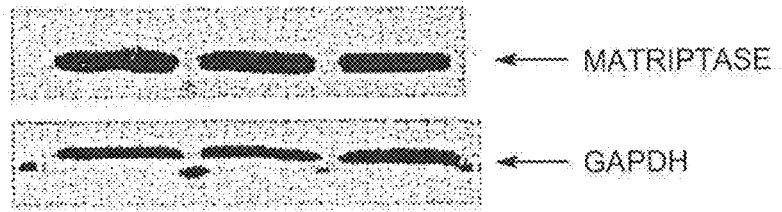
Figure 1D:

The levels of matriptase in cell lines of multiple myeloma were assessed (FIG. 1C). All three MM cells produced the protease.

Example 2

Preparation of DOX-Immunoconjugate

Monoclonal antibodies against matriptase (M24 or M69, obtained from CY Lin, University of Maryland, Baltimore, Md.; Lin C. Y., et al., J. Biol. Chem., 1999, 274 (26):18237-18242; Chen, Y. W., et al. J. Biol. Chem., 2010, 285 (41):31755-31762) was conjugated to DOX (Sigma) by using Protein-Protein Coupling kit (Invitrogen) according to the manufacture's instruction with some minor modification. Briefly, DOX was reacted with crosslinker SMCC (succinimidyl-4-(N-maleimidomethyl)cyclohexane-1-carboxylate) at a molar ratio (MR) between 1:3 and 1:1.5 (DOX:SMCC) for 1 hour at room temperature with constant stiffing. About 200 mg M24 mAb was reacted with SPDP (Succinimidyl 3-(2-pyridyldithio)-propionate) for 1 hour at room temperature followed by exchange of phosphate buffer using Centrifugal Filter Device (Ultrafree, Millipore). Alternatively, the mAb can be separated from free SPDP by gel filtration with Sephadex G50. DOX maleimide derivative was then conjugated to thiolated M24 or M69 mAb for 3 hours at room temperature followed by dialysis in the phosphate buffer to remove the free DOX. Gel filtration with Sephadex G50 can also be used to remove the uncoupled DOX if the scale of preparation is larger than one (1) gram of proteins. The molar ratio of protein to DOX is determined through measuring DOX by fluorescence and protein concentration.

Since DOX emits fluorescence by UV excitation, the coupling of DOX to the antibody was measured, based on the fluorescence generated by the immunoconjugate. M24-DOX at 1 gig/ml approximately has the same intensity of fluorescence as that of DOX at 25 nM. Hence, 1 molecule of the mAB is coupled with nearly 7 molecules of DOX.

TABLE 1

Summary of matriptase and HAI-1 expression in human lymphoma and leukemia cells

| Cell line | Cell Type | Disease/Source | Viruses* | Matriptase | HAI-1 |
|---|---|---|---|---|---|
| HL-60 | Promyeloblast | AML | — | — | +/— |
| Reh | Lymphoblast | ALL | — | — | +++ |
| Jurkat | T-Lymphoblast | ALL | — | — | + |
| SUP-T1 | T-Lymphoblast | LL | — | +++ | — |
| CCRF-CEM | T-Lymphoblast | ALL | — | — | +/— |
| CCRF-HSB-2 | T-Lymphoblast | ALL | — | — | ++ |
| MOLT-3 | T-Lymphoblast | ALL | — | — | — |
| MOLT-4 | T-Lymphoblast | ALL | — | — | — |
| CCRF-SB | B-Lymphoblast | ALL | EBV+ | — | +/— |
| RS4;11 | B-Lymphoblast | ALL | — | — | +/— |
| THP-1 | Monocyte | Acute Monocytic Leukemia | — | ++ | +/— |
| U-937 | Monocyte | Histiocytic Lymphoma | — | — | — |
| Hs 445 | B-Lymphoblast | HL | EBV+ | — | +/— |
| HuT 78 | Cutaneous T lymphocyte | Sezary Syndrome | — | — | ++ |
| Farage | B-Lymphoblast | EBV-transformed B cell lymphoma | EBV+ | +/— | — |
| RPMI 8266 | B-Lymphoblast | MM | — | ++++ | + |
| Daudi | B-Lymphoblast | BL | EBV+ | ++++ | — |
| Namalwa | B-Lymphoblast | BL | EBV+, SMRV+ | ++++ | — |
| Raji | B-Lymphoblast | BL | EBV+ | ++ | — |
| Ramos | B-Lymphoblast | BL | — | ++++ | — |
| ST486 | B-Lymphoblast | BL | — | ++++ | — |
| SU-DHL-4 | B-Lymphoblast | DLBL | — | ++++ | +/— |
| SU-DHL-6 | B-Lymphoblast | DLBL | — | ++++ | +/— |
| OCI-LY-3 | B-Lymphoblast | DLBL | — | ++++ | +/— |

Abbreviation:
AML, acute myelocytic leukemia;
ALL, acute lymphocytic leukemia;
BL, Burkitt's lymphoma;
DLBL, diffuse large B-cell lymphoma;
EBV, Epstein-Barr virus;
HL, Hodgkin's lymphoma;
LL, lymphoblastic leukemia;
MM, multiple myeloma;
SMRV, squirrel mokey retrovirus.

Example 3

Cytotoxicity of M24-DOX Toward Multiple Myeloma Cells

Figure 2:
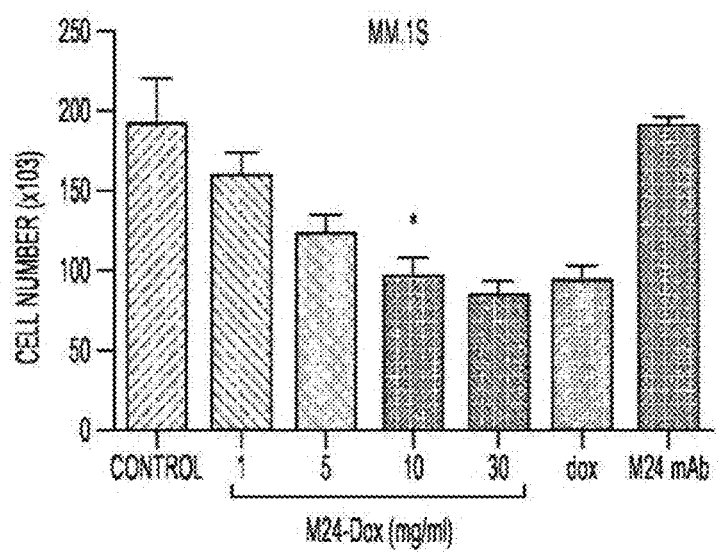
FIG. 2 illustrates cytotoxic effects of M24-DOX on MM cells. MM cells (1×105/well) in 24-well plates were treated with or without M24-DOX at varying concentration for 48 hours. Cell number was counted by Vi-Cell counter (Beckman). Error bars represent SEM. Statistical comparisons: *, significantly lower than control, p<0.036. Plotted values represent duplicates from three separate experiments.
Figure 2:
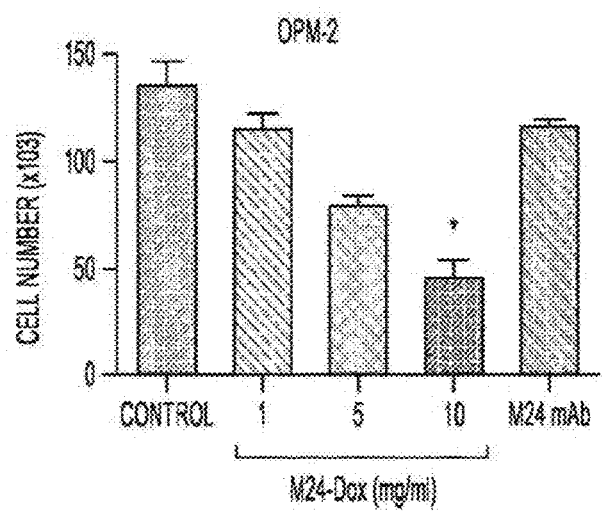
Figure 2:
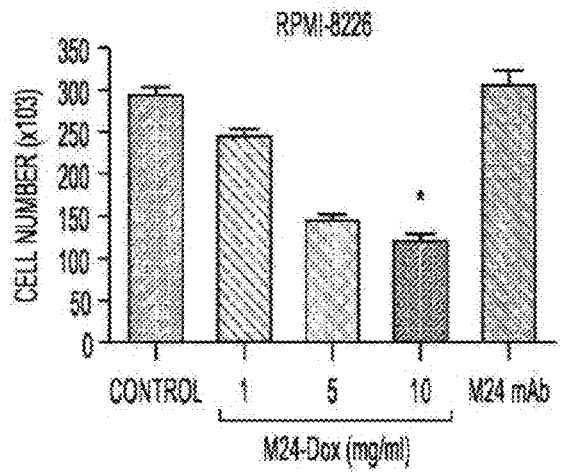

To assess the cytotoxic effect of the immunoconjugate, MM cells were treated with the conjugated DOX at various concentrations for 48 hours. The immunoconjugate inhibited cell proliferation in a dose-dependent manner. The EC50 of the immunoconjugate was 5 µg/ml (protein). This cytotoxic effect was also observed with treatment of free DOX at 200 nM. As the concentration of M24-DOX at 5 µg/ml is equivalent to 250 nM of free DOX based on the intensity of fluorescence, the potency of the conjugated DOX is therefore similar to the free drug. Exposure of the cells to unmodified antibody had no effect on cell growth, demonstrating that the M24-DOX induced cytotoxic effect is mediated through DOX activity. Two other MM cell lines including OPM-2 and RPMI-8226 were also tested for the cytotoxic activity of M24-DOX as shown in FIG. 2 where MM cells ($1 \times 10^5$/well) in 24-well plates were treated with or without M24-DOX at varying concentrations for 48 hours. Cell number was counted by Vi-Cell counter (Beckman).

Both types of cells also responded to the drug in a similar fashion as MM.1S did.

Example 4

Nuclear Localization of M24-DOX.

To demonstrate internalization of the immunoconjugate of DOX in MM.1S cells, fluorescent microscopy was used to trace the subcellular localization of M24-DOX after exposure of the cells to the drug for various periods of time. Following exposure of MM.1S cells to M24-DOX for varying periods of time, the cells were fixed and stained. The immunoconjugate was visualized by fluorescent microscopy. DAPI was used for nuclear staining.

Figure 3A:
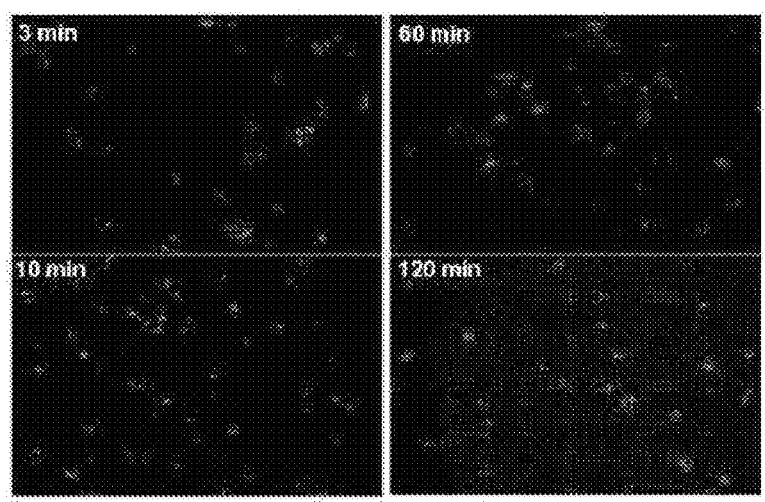
FIGS. 3A and B represent internalization of M24-DOX within cells. Following exposure of MM.1S cells to M24-DOX for varying periods of time, and the cells were fixed and stained. The immunoconjugate was visualized by fluorescent microscopy. DAPI was used for nuclear staining.
Figure 3B:
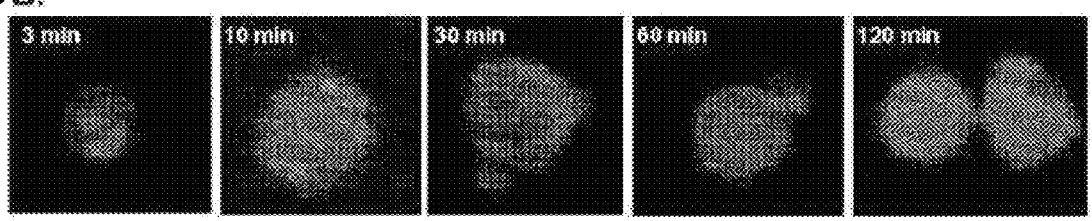

Trace amounts of nuclear fluorescence were detected in a small number of cells after 3 min exposure of the M24-DOX. Both the number of fluorescence stained cells and intensity of signal localizing in the nuclei were significantly increased with incubation times longer than 30 min (FIG. 3A). The pictures with higher magnification revealed swelling of nuclei of cells exposed to the drug for 60 min or longer, indicative of typical DOX-induced apoptosis (FIG. 3B). These data indicate that following binding to the antigen, the immunoconjugate was rapidly internalized and significant nuclear localization of DOX was observed after 10 min of treatment.

Example 5

Tolerance of Bone Marrow-Derived Mesenchymal Stem Cells (MSCs) Toward M24-DOX.

Figure 4A:
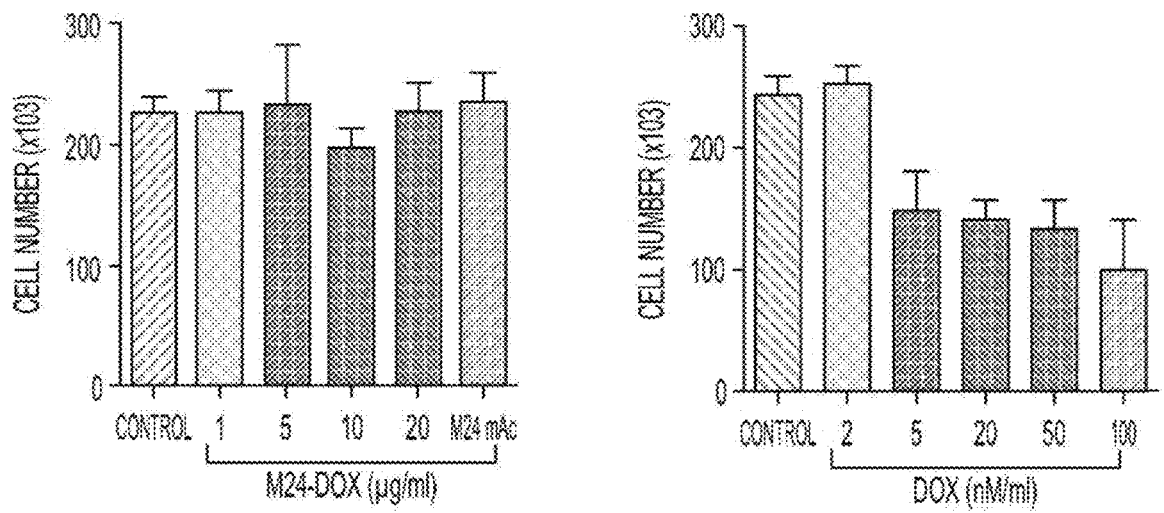
FIGS. 4A-C illustrate reduced cytotoxicity of M24-DOX to normal marrow mesenchymal cells. Bone marrow-derived mesenchymal stromal cells (5×104/well, 24-well plates) were treated with M24-DOX or free DOX at varying concentrations for 4 days. Cell numbers were determined by Vi-Cell counter. (A) shows that M24-DOX lacks cytotoxicity to stromal cells; (B) shows reduced cytotoxicity to cardiomyocytes; and (C) shows comparison of M24-DOX with DOX and control.
Figure 4B:
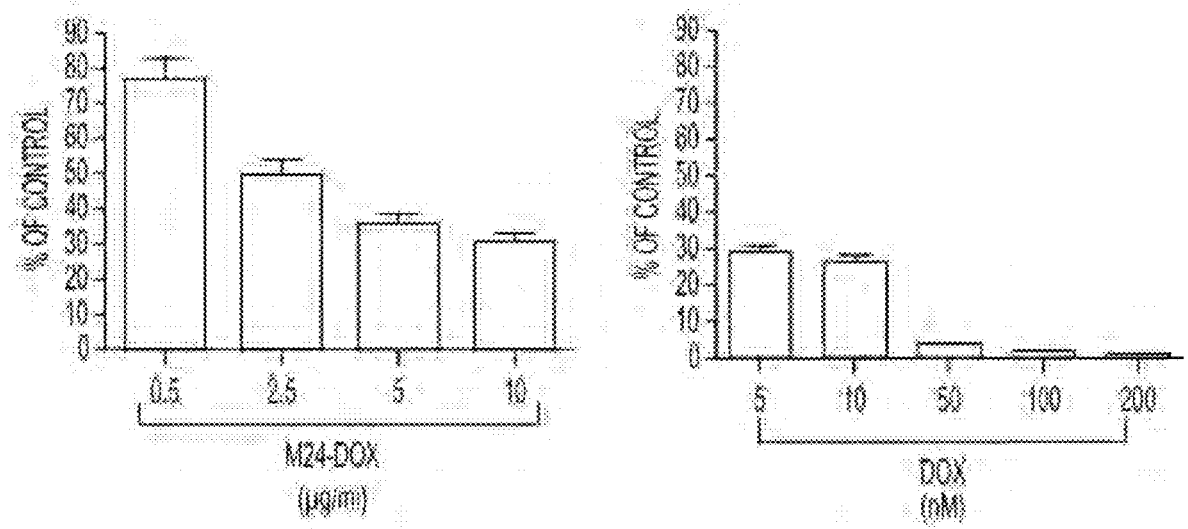
Figure 4C:
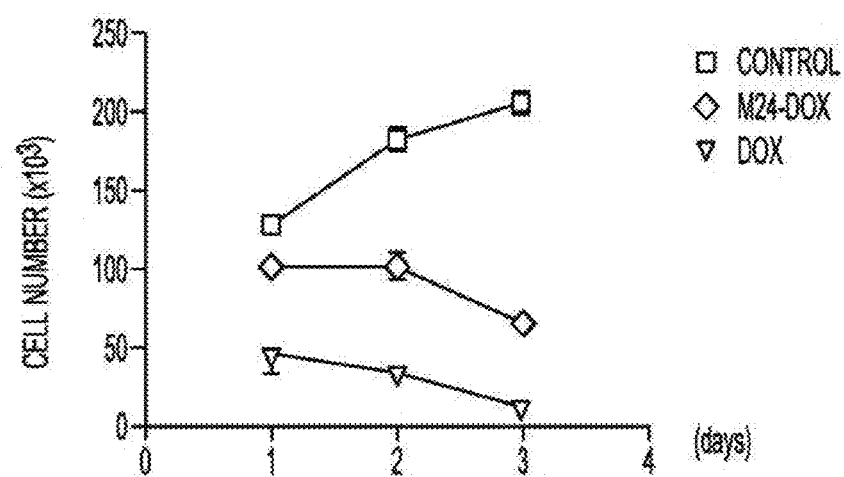

Human bone marrow-derived MSCs, which lack matriptase expression, were used as a control to determine the cytotoxic selectivity of M24-DOX as shown in FIG. 4 where bone marrow-derived mesenchymal stromal cells ($5 \times 10^4$/well, 24-well plates) were treated with M24-DOX or free DOX at varying concentrations for 4 days. Cell numbers were determined by Vi-Cell counter.

The MSCs were insensitive to the immunoconjugate at a concentration as high as 20 µg/ml, whereas free DOX was able to significantly inhibit cell proliferation at 5 nM. Expression of matriptase is mainly restricted to epithelial cells in normal tissues. Absence of this protease in cardiomyocytes indicates that M24-DOX will exhibit significantly reduced cardiotoxicity.

Example 6

Targeting Active Matriptase

Figure 5:
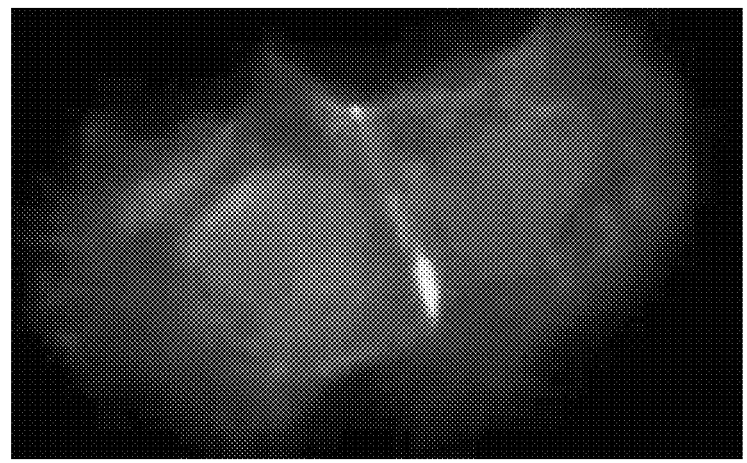
FIG. 5 illustrates activation of matriptase in MM cells induced by thalidomide. MM cells (MM.1S) were treated with varying concentrations of thalidomide as indicated for 24 hours followed by Western analyses to detect the activation of matriptase using a specific monoclonal antibody (M69) to the active form of the enzyme. The latent form of the protease was also detected using a mAb (M24) to the inactive form enzyme. GAPDH served as control.
Figure 5:
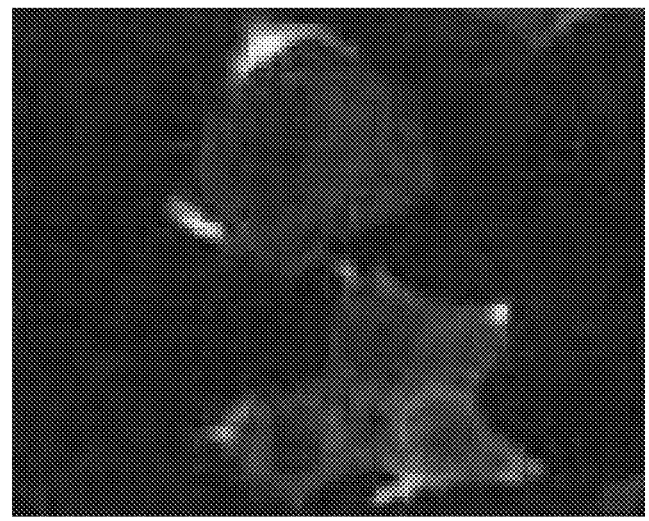

DOX was also conjugated with another matriptase mAb (M69) that specifically binds to the active two-chains of the enzyme. While active matriptase levels were found in most breast tumors, the active form of the protease is barely detectable in the normal tissues of the mammary gland (FIG. 5). These data indicate that the DOX-conjugate with M69, referred to as M69-DOX, offers additional selectivity in targeting tumors expressing activated matriiptase with regard to toxicity toward normal tissues. As epithelial tissues express matriptase, the toxicity of M24-DOX toward the healthy tissues is a concern. For instance, a previous DOX-conjugate called BR96 targeting Lewis-Y antigen in carcinoma cells failed in the phase II trial due to considerable gastrointestinal (GI) toxicity (Tolcher, A. W., et al., J. Clin. Oncol., 1999, 17: 478-484) In contrast to the expression of latent form of matriptase in epithelial tissues, the level of the active form of this protease is hardly detectable by immunohistochemistry. Hence, M69-DOX is less toxic to epithelia.

Example 7

Enhanced Cytotoxic Effects of M69-DOX by Thalidomide

Figure 6A:
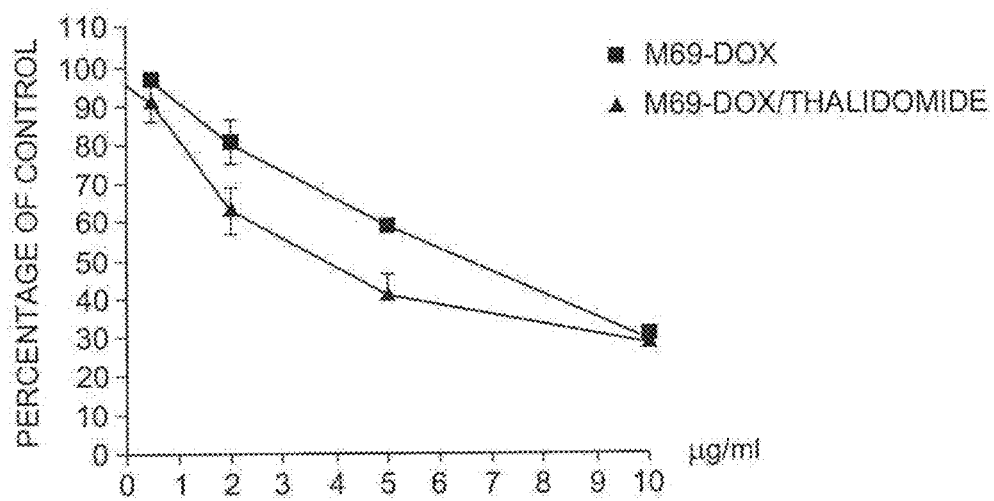
FIGS. 6A and B illustrate that thalidomide sensitizes MM cells to M69-DOX, but not M24-DOX: (A) comparison of treatment of MM cells by M69-DOX alone with the M69-DOX/thalidomide combination treatment; and (B) comparison of treatment of MM cells by M24-DOX alone with the M24-DOX/thalidomide combination treatment.
Figure 6B:
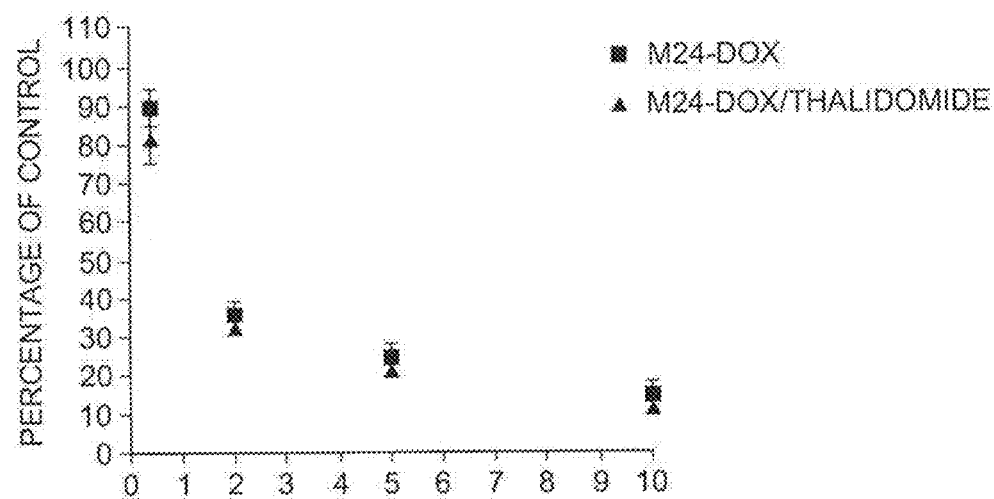

Thalidomide is a therapeutic for multiple myeloma treatment, and the combination of thalidomide and dexamethasone is one of the most common regimens for treatment of patients with multiple myeloma, with an response rate of up to 60-70% (Denz, U., Eur. J. Cancer., 2006, 42:1591-1600; Gieseler, F., et al., Thromb. Haemost., 2008, 99: 1001-1007). The efficacy of both DOX-conjugates in combination with current MM therapeutics such as thalidomide was tested. M69-DOX by itself alone was less potent than M24-DOX. Surprisingly, inhibition of cell proliferation by M69-DOX treatment was significantly augmented by thalidomide, whereas the inhibitory activity of M24-DOX was not altered (FIG. 6A-B). This enhanced inhibition by M69-DOX combined with thalidomide appeared to be synergistic, as thalidomide alone had no effect on MM cell proliferation (FIG. 6A). Therefore these studies show that thalidomide resulted in enhanced inhibition of proliferation.

Example 8

Matriptase Activation Induced by Thalidomide in MM Cells

Figure 7:
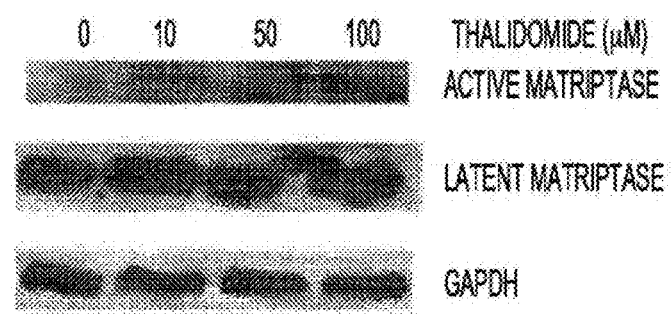
FIG. 7 illustrates activation of matriptase in MM cells induced by thalidomide. MM cells (MM.1S) were treated with varying concentrations of thalidomide as indicated for 24 hours followed by Western analyses to detect the activation of matriptase using a specific monoclonal antibody (M69) to the active form of the enzyme. The latent form of the protease was also detected using a mAb (M24) to the inactive form enzyme. GAPDH served as control.

To examine the increase in cytotoxicity that resulted with the thalidomide and M69-DOX conjugate we measured the effect of thalidomide on expression of activated matriptase. Activation of matriptase in MM cells was markedly enhanced after 24-hour treatment with 50 µM thalidomide (FIG. 8) Thalidomide is known to exert antiangeiogenic activity by interfering with the interaction between MM and bone marrow stromal cells, at least in part, through inhibition of VGEF production. While thalidomide appears to have little effect on the cell proliferation of MM cells (FIG. 7A-B), its ability to activate matriptase is an important novel finding, suggesting a novel approach to exploit the response of MM cells to thalidomide treatment by targeting active matriptase-positive myeloma cells with the M69-DOX conjugate.

Example 9

Figure 8:
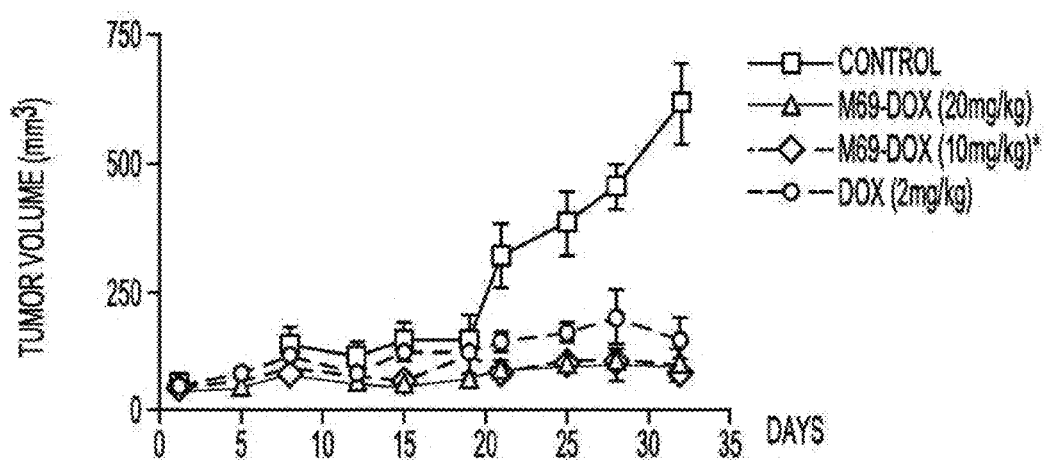
FIG. 8 illustrates the M69-DOX conjugate targeting active matriptase inhibited breast tumor growth in vivo, comparing treatment by M69-DOX at 10 mg/Kg and 20 mg/Kg doses with treatment by DOX at 2 mg/Kg dose and the control.

Inhibition of Breast Tumor Growth by M69-DOX Targeting Active Matriptase In Vivo To assess the efficacy of M69-DOX to suppress tumor growth in vivo, a human breast xenograft tumor model was used. NOD/SCID mice bearing breast tumors (MDA-MB468) were treated twice weekly with M69-DOX at either 20 or 10 mg/kg, as well as treated with DOX at 2 mg/kg. While the tumor sizes of the mice in the untreated control group were markedly increased at the third week, tumor growth in the mice treated with M69-DOX at either dose and treated with DOX was significantly abolished during the entire treatment course (FIG. 8). As a single mAb was attached with 7 molecules of DOX, a dose at 10 mg/kg of M69-DOX is equivalent to 0.035 mg/kg of DOX administered. These results demonstrate strong potency and efficacy of DOX conjugate targeting activated matriptase to treat breast tumors in vivo.

Figure 9:
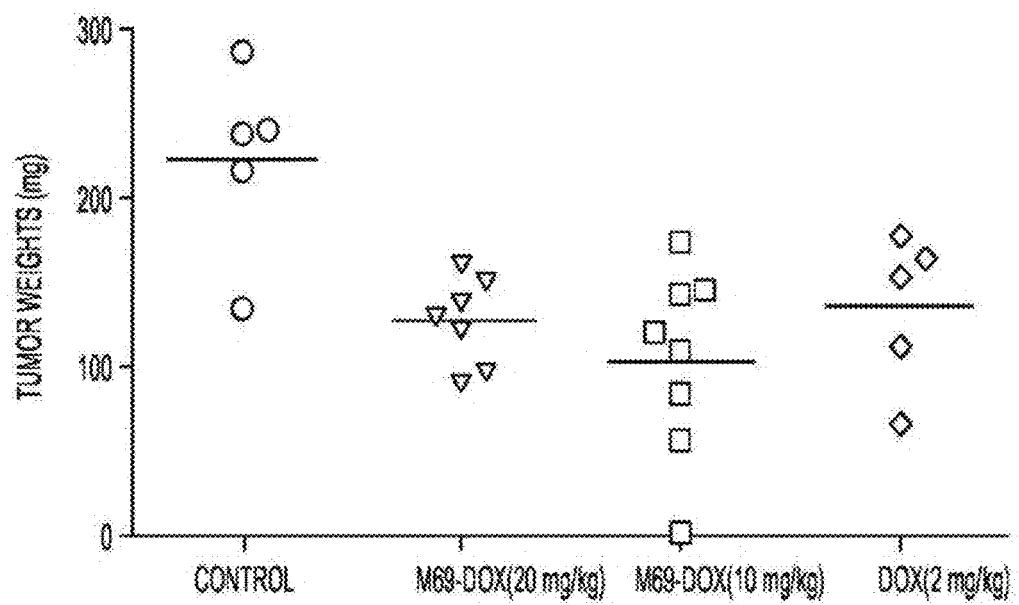
FIG. 9 illustrates reduction of the tumor weight by M69-DOX at 10 mg/Kg and 20 mg/Kg doses in comparison with treatment by DOX at 2 mg/Kg dose and the control.

Reduced Weights of Tumor Masses in Mice Treated with M69-DOX. At the end of the treatment course, the tumor masses were collected from the experimental mice, and were weighed. The average weights of tumors from the groups treated with M69-DOX at either dose as well as treated with DOX were reduced to about 50% of the one from the untreated control group (FIG. 9). Significant reduction in tumor weights by M69-DOX further confirms the efficacy of site-directed delivery of DOX to tumor cells expressing activated matriptase.

Minimal Toxicity by M69-DOX Treatment

Figure 10:
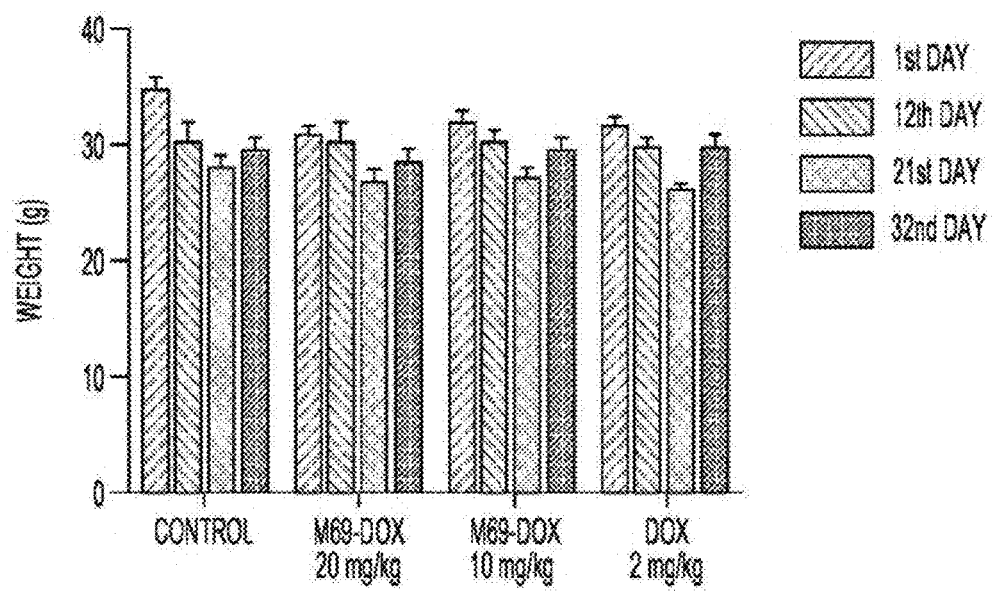
FIG. 10 illustrates the average weights of the mice during the treatment by M69-DOX at 20 mg/Kg and 2 mg/Kg doses or DOX at 2 mg/Kg dose in comparison with the control.

The average weights of mice treated with either M69-DOX or DOX were not markedly reduced (less than 15% loss) compared to those from untreated control group, indicating that the M69-DOX at such doses was well tolerated (FIG. 10). The dosage at 20 mg/kg of M69-DOX did not lead to noticeable toxicity, indicating that the drug dose can be escalated to reach the maximum tolerant dose.

Example 10

Coupling of MMAE Via a Releasable Linker to a M69 mAb to Form a Conjugate: M69-MMAE.

Figure 18:
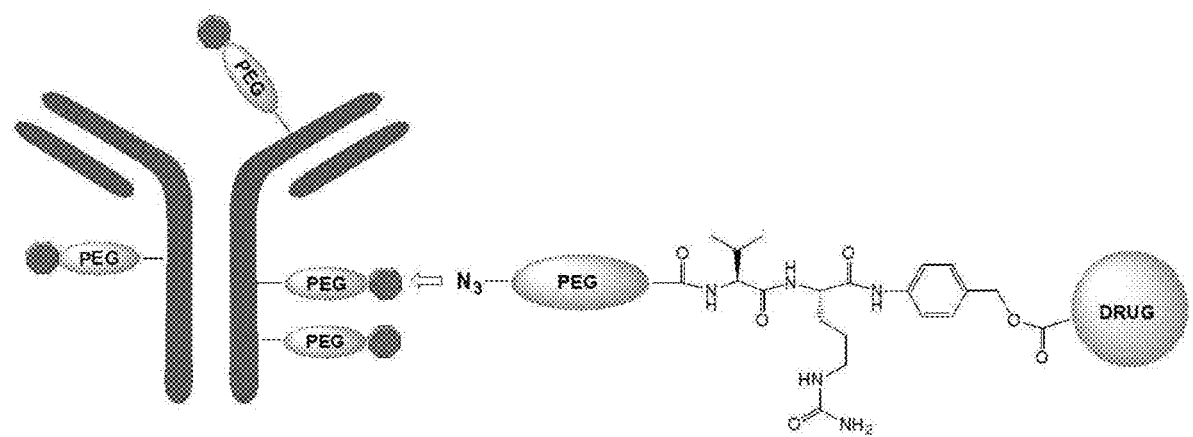
FIG. 18 illustrates overall design of the ADC assembly used in Examples 11-13. Octagons represent DBCO units, arrow represent copper-free click chemistry.
Figure 19:
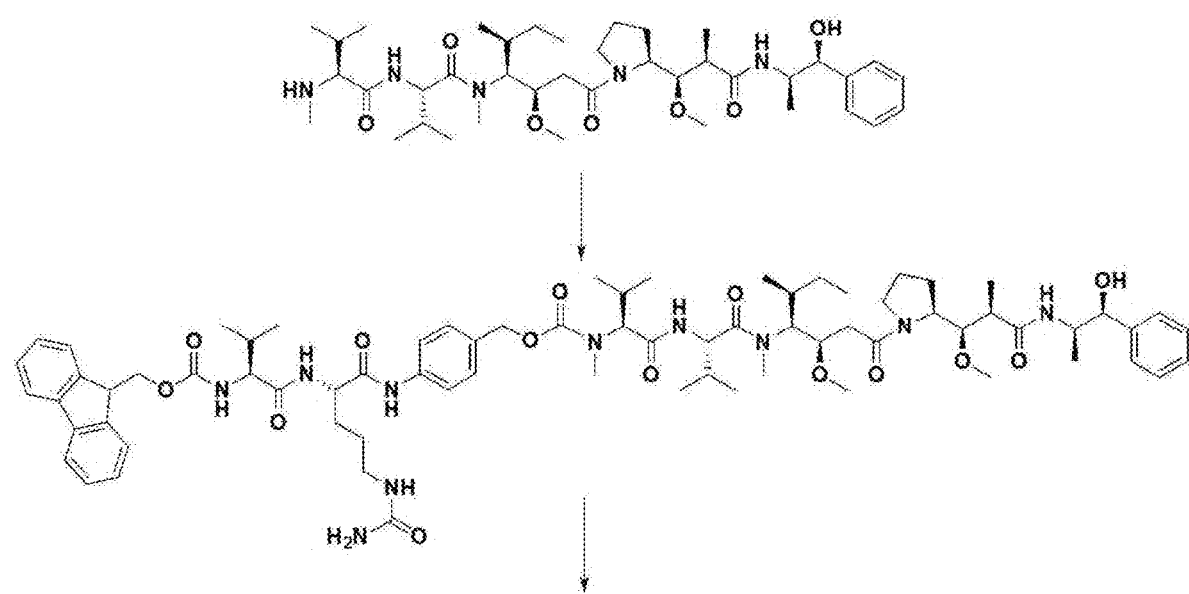
FIG. 19 illustrates the chemical synthesis of Azido-PEG$_4$-Val-Cit-PABA-MMAE construct used in Examples 11-13.
Figure 19:
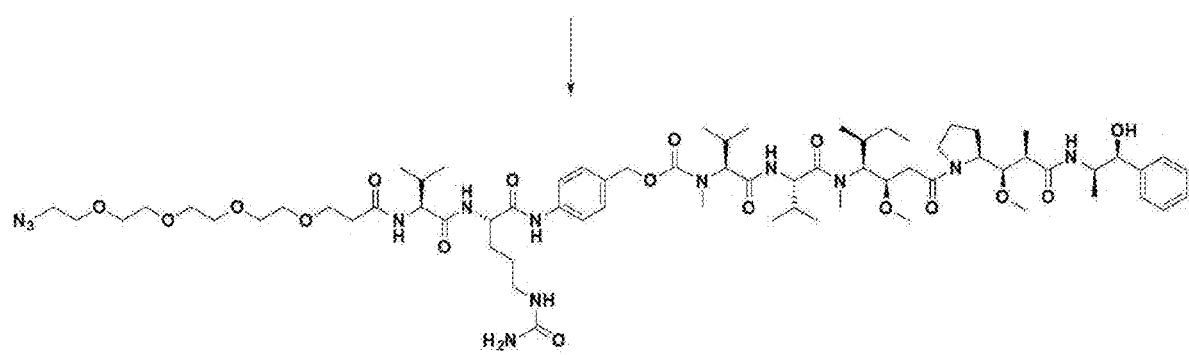

MMAE was coupled to M69 to form an immunoconjugate as described here. The releasable linker technology was based on Seattle Genetics' Valine-Citrulline-PABA linker, the original Cathepsin B cleavable linker, as described in Bioconjugate Chem. 2002, 13:855-869; Blood 2003, 102:1458-1465; Nature Biotech., 2003, 21:778-784, all of which are hereby incorporated by reference in their entirety. The Valine-Citrulline-p-aminobenzylalcohol carbamate linker was modified by (i) a two-stage PEGylation, (ii) conjugation via copper-free click chemistry, and (iii) acylating lysine side chains of the mAb instead of cysteine sulfhydryl-maleimide coupling. The overall design of the ADC assembly is depicted in FIG. 18. Chemical synthesis of Azido-$PEG_4$-Val-Cit-PABA-MMAE construct was as depicted in FIG. 19. The present design improved this linker platform using copper-free click chemistry using DBCO and $N_3$, enabling the performance of crucial drug loading steps in a stoichiometrically controlled manner under very mild conditions. Lysine side chains were utilized to conjugate the linker-drug ligand onto the surface of the antibodies instead of using temporarily reduced sulfhydryl groups of cysteine residues (FIG. 11). Since this approach does not affect disulfide brides between cysteines, the anti-matriptase antibodies remain structurally intact during the conjugation procedure, eliminating the problem with loss of activity by misfolded/dissociated antibody chains. Furthermore, lysine side chains are readily available on the surface of the mAb, so there was no need to reduce Cys-Cys disulfide bridges eliminating the problem of structural destabilization of the mAb and mismatched disulfide bond formation upon oxidation following maleimide conjugation. Appropriate analytical procedures (HR-MALDI-TOF mass spectrometry) demonstrated that recent batches of immunoconjugates meeting industrial standards (FIG. 11). A further advancement was achieved by using PEG spacers in the drug-linker part of the conjugate on both precursors of the click chemistry that facilitates the use of even very hydrophobic drug molecules. The PEG chains were long enough to keep the mAb and the drug separate, decreasing the probability of unspecific drug and antibody interactions, and the $PEG_5$-$PEG_4$ configuration of the linker compensated the hydrophobicity of tetracyclic system resulted by the copper-free click chemistry. The cytotoxic compound selected was monomethyl auristatin E, or MMAE. The flexibility and length of the PEGylated linker provide high accessibility for the Cathepsin B to cleave and release MMAE. The conjugation reactions were monitored by MALDI-TOF mass spectrometry showing 7000 Da increase of the average MW that corresponds to 3.5 drugs linked to each mAb molecule.

To demonstrate the cytotoxic potency of M69-MMAE, the in vitro cytotoxic efficacy of the immunoconjugates toward a triple negative breast cancer, MDA-MB468, was assessed. The breast cancer cells were sensitive to the MMAE-linked immunoconjugate with an IC50 of 3.4 μg/ml. As each M69 molecule contained an average of 3.5 molecules of MMAE (FIG. 11), the sensitivity to MMAE in the conjugate was 1.6 nM. This experiment also demonstrated that the immunoconjugate is internalized and toxin released intracellularly.

Example 11

In Vitro Cytotoxicity of M69-MMAE Immunoconjugates

To evaluate the in vitro cytotoxicity of the M69-MMAE immunoconjugates as described in Example 10, tumor cells such as TNBC (MDA-MB-468, MDA-MB-231 and BT549), prostate (DU145 and PC3), pancreas (PANC1 and MiaPacal), NSCL (H322 and H1299), Ovary (OVCAR5), stomach (AGS), and Mantle cells lymphoma (Mino, Jeko, Maver and Z138) cancers were exposed to M69-MMAE immuno-conjugates with various concentrations as indicated. After 72 hours of continuous exposure to the immunoconjugate, cytotoxicity was assessed by MTS (Promega) assay as follows: MTS colorimetric assay (CellTiter 96 from Promega) was performed according to the manufacturer's protocols. Cancer cells were plated in 96-well plates at 8000 cells/well, and were exposed to a graded titration of M69-MMAE for 72 hours at 37° C. The percentage viability, relative to untreated control wells, was plotted versus immunoconjugate concentration. Results of each study are the average of quintuplicate determinations. The values of IC50 of M69-MMAE against these cells were summarized in Table 2 below. IC50s of M69-MMAE toward the indicated tumor cells were determined by a MTS colorimetric method with 96-well plates as described. The IC50 values were presented as means (μg/mL)±SD of the ADC as well as equivalent nM of MMAE concentration considering that the ADC has a stoichiometric ration of 3.5 MMAE/mAb.

Figure 14:
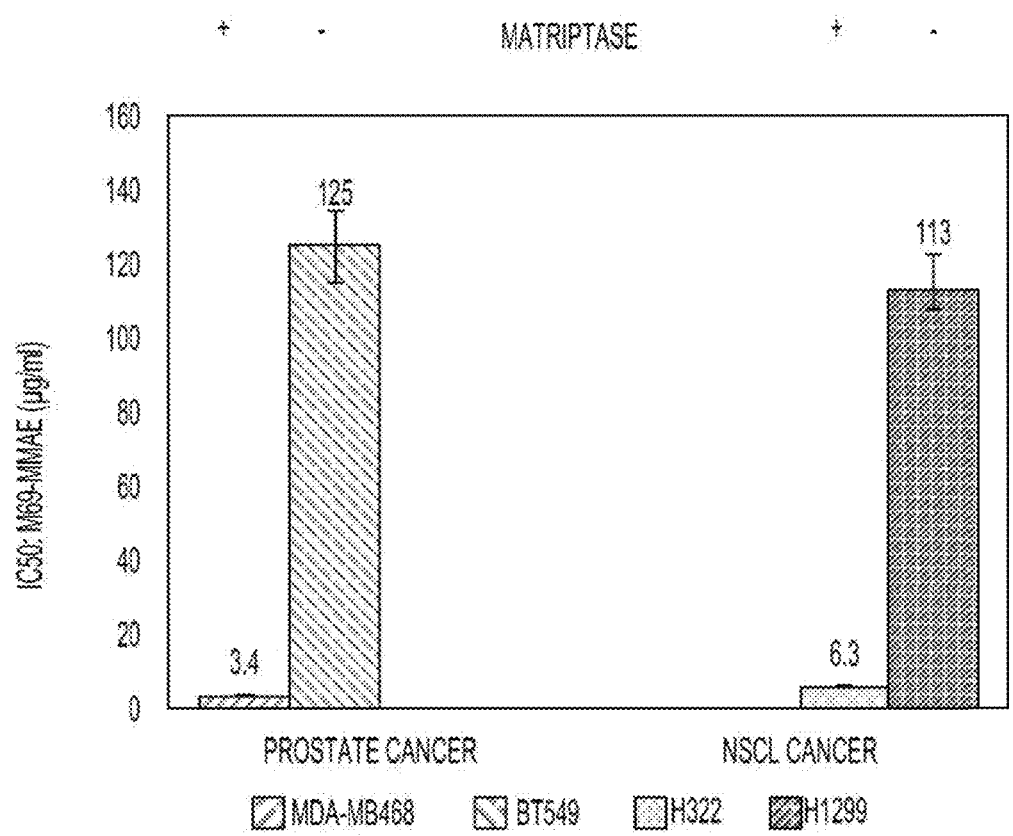
FIG. 14 illustrates IC50s of M69-MMAE immunoconjugates toward matriptase-positive and negative cells in prostate cancer cells and non-small cell lung (NSCL) cancer cells

These cancer cells were sensitive to the immunoconjugate with IC50s ranging from low single digit to tens gig/ml of the conjugate. While gastric cancer cells, AGS, were very sensitive to the MMAE conjugate with IC50 as low as 1.5 μg/mL, Mantle cell lymphoma cells, Maver, required a higher concentration (30 μg/mL) of the conjugate to reach IC50. As about three molecules of MMvAE are attached to each mAb, the IC50 values were also presented as carried MMAE concentration as indicated. IC50s of mariptase-negative cells such BT549 and H1299 were also obtained to demonstrate selective cytotoxicity of the conjugate (FIG. 14). The ratios of IC50s of matriptase-positive and -negative cells were quite significant ranging from 18 to 48 (11299 vs H322, and BT549 vs MDA-MB231), suggesting that the degree of selectivity of M69-MMAE should offer benefit of minimized side effects.

TABLE 2

IC50s of M69-MMAE toward various cancer cells

| Cancer Type | Cell Line | IC50s (µg/mL), M69-MMAE conc. | IC50s (nM), MMAE conc. |
|---|---|---|---|
| Breast | MDA-MB231 | 2.6 ± 0.09 | 59.2 |
|  | MDA-MB468 | 3.4 ± 0.30 | 77.5 |
|  | BT549 | 125.0 ± 10.25 | 2847.5 |
| Prostate | DU145 | 8.0 ± 3.4 | 182.2 |
|  | PC3 | 6.8 ± 0.65 | 154.9 |
| Non-small cell Lung | H322 | 6.3 ± 0.20 | 143.5 |
|  | H1299 | 113 ± 5.20 | 2574.1 |
| Ovary | Ovcar5 | 16.0 ± 0.4 | 364.5 |
| Pancreatic | PANC1 | 12.0 ± 0.06 | 273.4 |
|  | MiaPacal | 8.0 ± 0.83 | 182.2 |
| Stomach | AGS | 1.5 ± 0.03 | 34.2 |
| Mantle Cell Lymphoma | Mino | 6.2 ± 0.18 | 141.2 |
|  | JeKo-1 | 13.9 ± 3.9 | 316.6 |
|  | Z138 | 19.0 ± 1.9 | 432.8 |
|  | Maver | 30.0 ± 2.8 | 683.4 |

Example 12

In Vivo Xerograph Studies Involving M69-MMAE Immunoconjugates

Figure 13:
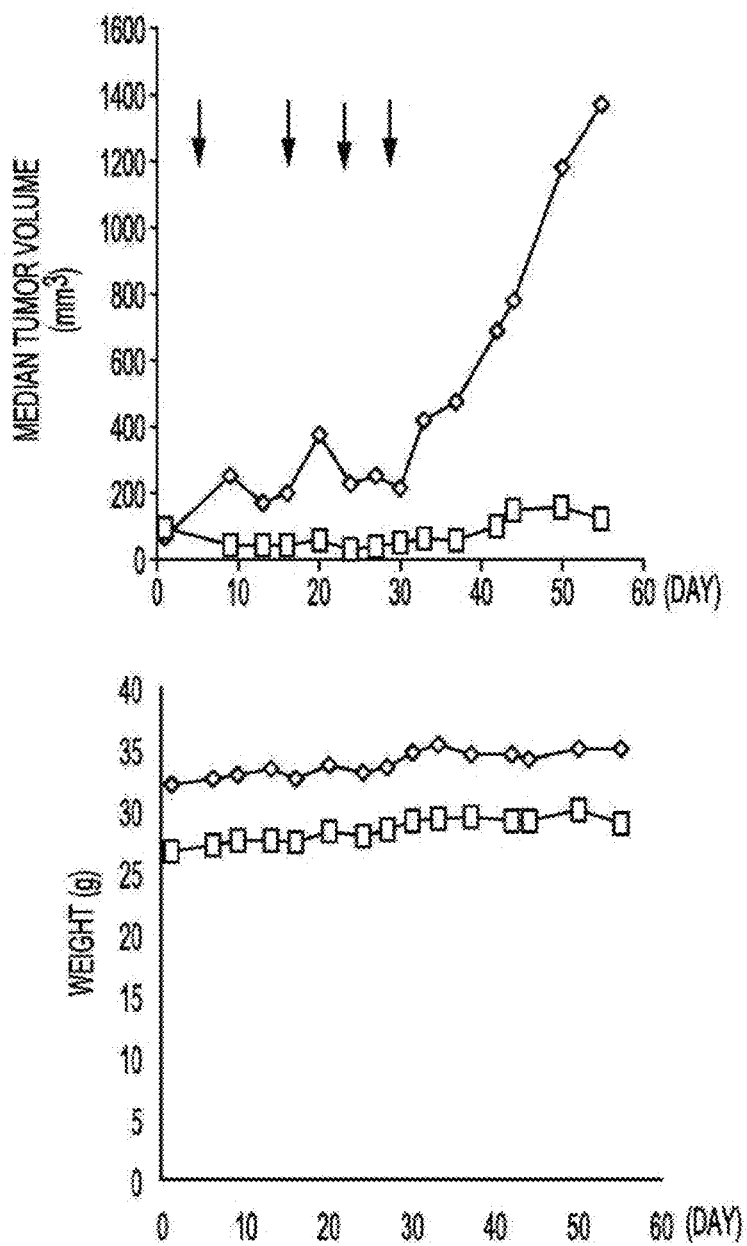
FIG. 13 illustrates how matriptase-MMAE conjugate inhibits growth of the TNBC MDA-MB-468 without causing weight loss or signs of toxicity. Mice were inoculated s.c. with 10 million tumor cells in the right flank. When the tumor was palpable (100-200 mm$^3$) mice were randomized into two groups (n=6) and treated at the times indicated by the arrows with the immunoconjugate administered i.p. 5 mg (M69-MMAE)/kg (square shapes, bottom line). Control mice received saline (diamond shapes, top line).

A pilot xenograft study was conducted using the M69-MMAE immunoconjugate as described in Example 10. A toxicity study in nude mice with the mouse conjugate (N=6), administered i.p. weekly x3, at 10 mg/kg was conducted prior to testing the chimeric M69-MMAE conjugate. There was no weight loss or signs of toxicity, indicating that the construct was stable and did not target normal tissues. Based on this information, mice bearing the human triple negative breast tumor MDA-MB-468 were treated with M69-MMAE immunoconjugates. FIG. 13 shows that the conjugate has potent anticancer activity against this triple negative breast cancer, importantly; there was no weight loss or other evidence of toxicity in the animals, indicating that no significant free drug was released into the circulation from the conjugate. As this is a mouse antibody in the mouse, an antibody response to matriptase would not be expected. FIG. 14 shows the results of median tumor volume (in mm$^3$) for the control mice and those mice treated with M69-MMAE immunoconjugates; a significant increase in tumor size was observed in the control group relative to those treated with M69-MMAE.

Figure 15A:
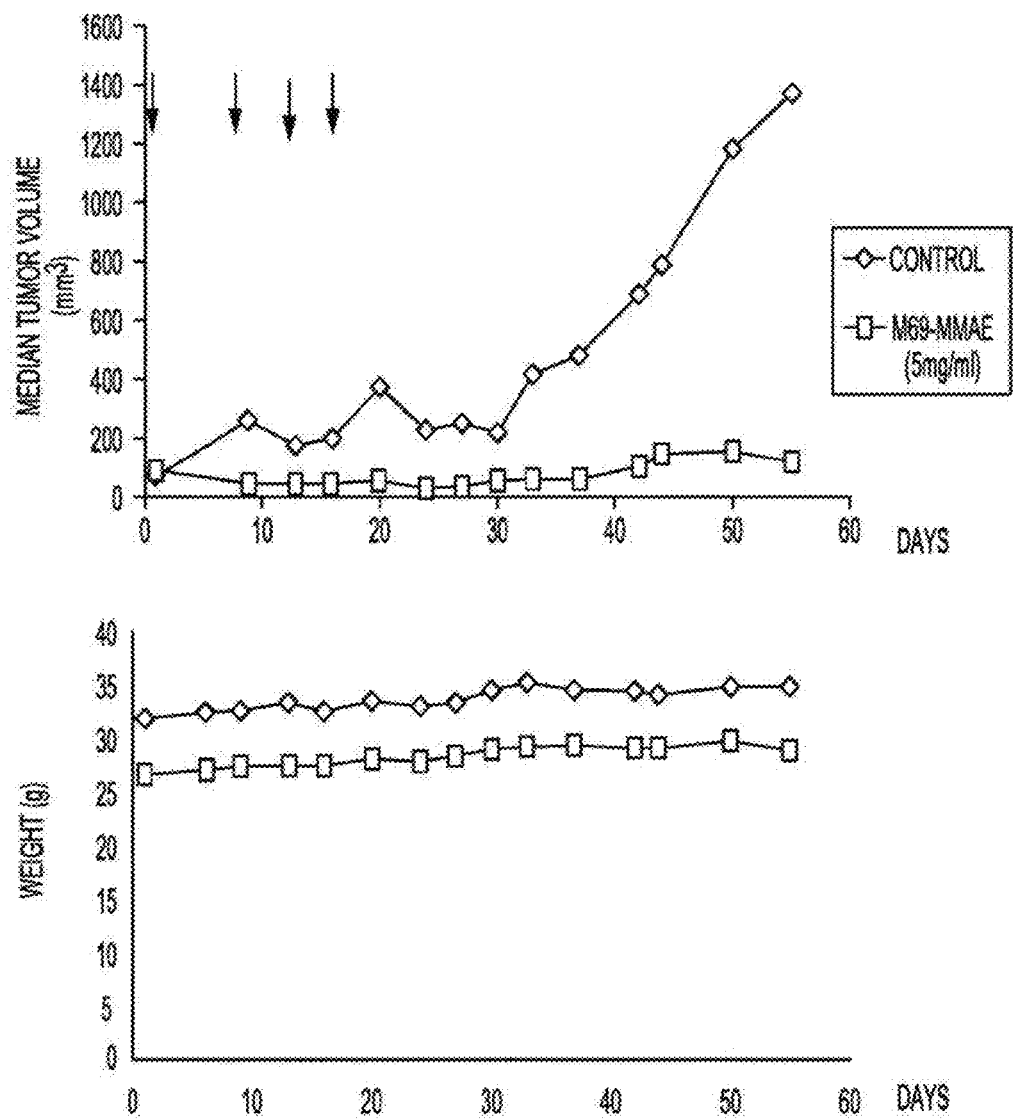
FIG. 15A-C illustrates in vivo efficacy of M69-MMAE immunoconjugates toward triple-negative breast cancer (MDA-MB-468) (A) non-small cell lung (NSCL) cancer cells (H322) (B), and prostate cancer cells (DU145) (C). Diamond shape represent control, square shaped line represent M69-MMAE at 5 mg/mL, and for (B) the triangle shaped line represents M69-MMAE at 1 mg/mL. Arrows indicate times treated with the immunoconjugate.
Figure 15B:
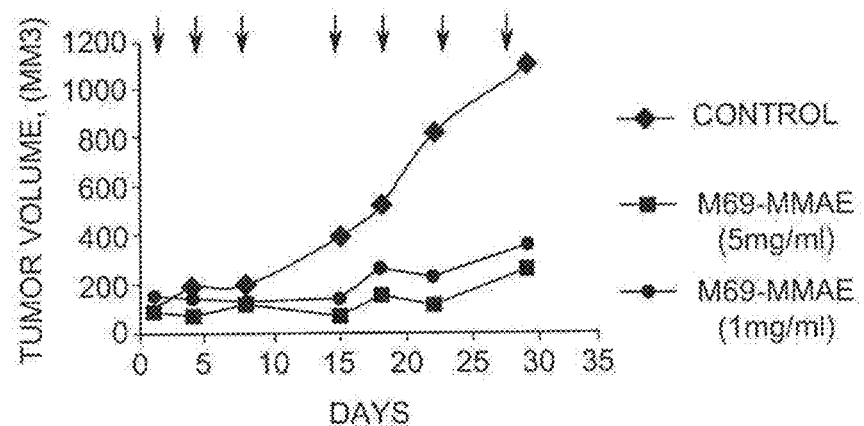
Figure 15C:
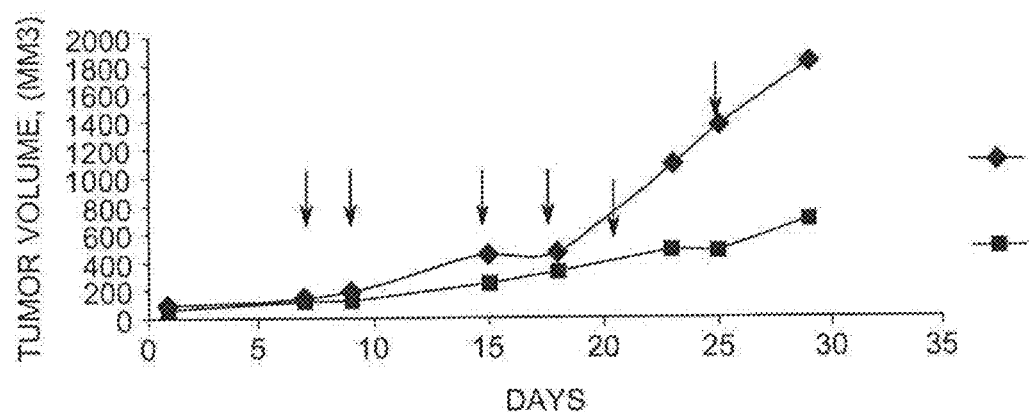

Based on these results, further in vivo xenograft studies were warranted. These additional xenograft studies were performed to assess the in vivo efficacy of M69-MMAE toward various types of cancer. TNBC (MDA-MB-468 and MDA-MB-231), prostate cancer cells (DU145), and NSCL cancer cells (H322) were harvested in the exponential growth phase with trypsin solution and washed with PBS. Viable cells (7×10$^6$) in 100 µl of PBS suspension were mixed with 100 W of Matrigel (BD Biosciences) and injected subcutaneously at right flank of the animals. Once the tumors were palpable, the mice were randomized into treatment groups of six mice each. The animal received intraperitoneal injection of 5 mg/kg M69-MMAE or 1 mg/kg M69-MMAE twice weekly. Tumor size was measured with digital calipers and was calculated using the formula $4/3\pi \times length \times width^2$. The results showed effective regression of the triple-negative breast tumors (MDA-MB468 and MDA-MB-231) by the treatment of M69-MMAE (FIG. 15A). Tumor growth of both NSCL and prostate cancer mice was also greatly abated compared the one of the vehicle controls (FIG. 15B,C). The antitumor activity of M69-MMAE remains effective at the dose as low as 1 mg/kg (FIG. 15B). Surprisingly, there was no weight loss or other evidence of toxicity in the animals, indicating that no significant free drug was released into the circulation from the conjugate (FIG. 15A).

Example 13

Figure 16:
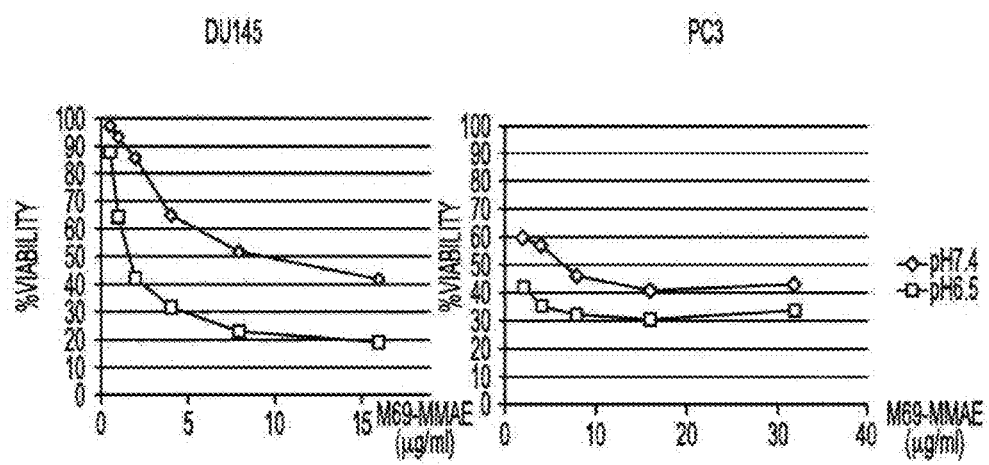
FIG. 16 illustrates that DU145 and PC3 cells were exposed to M69-MMAE at varying concentrations as indicated for 72 hours under pH7.4 (diamond shape) or pH6.5 (square shape), HCl-acidified, medium. Viability was measured as percentages of viability of cells in control wells with respective medium.

Prostate Cancer Cells are More Sensitive to M69-MMAE Under Acidic Extracellular pH Activation of matriptase is induced by acidosis. Thus, cancer cells expressing activated matriptase are more sensitive to the cytotoxic effect of the M69-MMAE immunoconjugates as described in Example 10 under acidic condition due to increased antigen levels. This was proven by an experiment wherein both DU145 and PC3 prostate cancer cells become more sensitive to the immunoconjugate with HCl-acidified medium at a pH 6.5. The IC50s were significantly reduced from 8 to 1 µg/ml, and from 6.8 to less than 2 µg/mL for DU145 and PC3 cells respectively (FIG. 16). The exposures to acidic condition were only maintained about 30 min, as the carbonate buffering of the medium gradually brought up the pH after 1 hour in CO2 incubator.

Tumor microenviroments are characterized by acidic extracellular pH (pHe) due to accumulation of lactic acid resulted from high glycolic activity of cancer cells regardless of oxygenation condition, a phenomena also called "Warburg effect". Accumulating evidence show that high lactate levels is a main driving force for invasive and metastatic progression of tumor as well as tumor recurrences. Thus, M69-MMAE allow selective delivery of a potent toxin to cancer cells, such as prostate cancer cells, that express activated matriptase in an acidic environment.

Example 14

Taxatere-Resistant Prostate Cancer Cells (PC3R) are Sensitive to M69-MMAE

Figure 17:
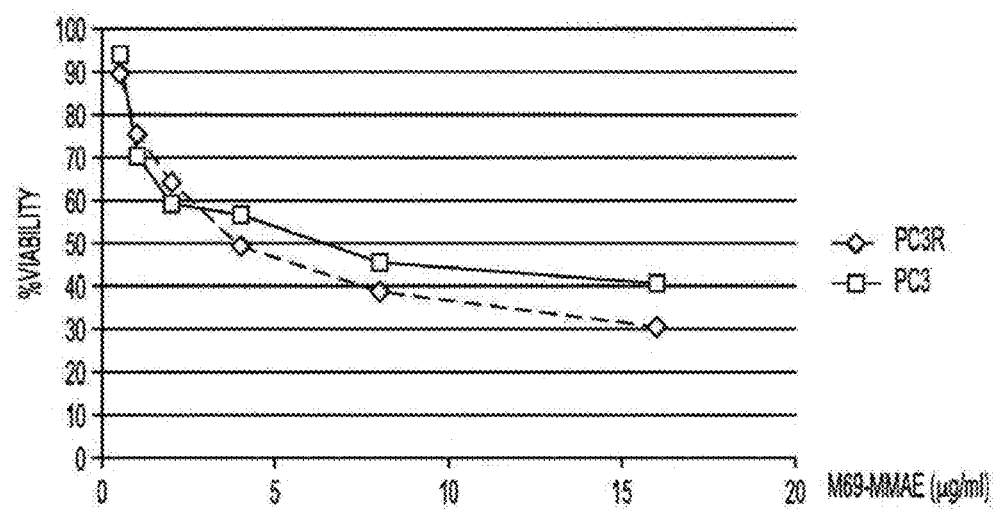
FIG. 17 illustrates that Taxotere-resistant and -sensitive prostate cancer cells, PC3R (diamond shaped) or PC3 (square shaped), were treated with M69-MMAE at varying concentrations as indicated. Viability was measured as percentages of viability of cells in control wells.

To determine in vitro efficacy of the M69-MMAE immunoconjugates as described in Example 10 to chemo-resistant cancer cells, taxtere-resistant cells were treated with the conjugate. Despite the resistance to mitotic inhibition, PC3R cells were as sensitive as the parental PC cells to MMAE conjugate (FIG. 17). This highlights how M69-MMAE is an effective treatment for patients with chemo-resistant prostate cancer.

It will be understood by those of skill in the art that numerous and various modifications can be made without departing from the scope and spirit of the present invention. Therefore, it should be understood that various embodiments of the invention described herein are illustrative only and not intended to limit the scope of the invention. All references cited herein are incorporated by reference in their entirety.

The invention claimed is:

1. A method of treating a malignancy comprising cells that express matriptase, the method comprising administering to a subject in need of such a treatment a therapeutically effective amount of a composition comprising an immunoconjugate that comprises an anti-matriptase antibody or antigen-binding fragment thereof and a cytotoxic agent, wherein:
    the cytotoxic agent is selected from the group consisting of monomethyl auristatin E (MMAE), monomethyl auristatin F (MMAF), and auristatin PE;

the anti-matriptase antibody or the antigen-binding fragment thereof selectively binds activated matriptase expressed on tumor cells, the anti-matriptase antibody or the antigen-binding fragment thereof is M69 monoclonal antibody or an antigen-binding fragment thereof, or is a chimeric or humanized form thereof; and the malignancy comprises a hematological malignancy selected from the group consisting of acute lymphoblastic leukemia (ALL), acute myelogenous leukemia (AML), chronic lymphocytic leukemia (CLL), small lymphocytic lymphoma (SLL), chronic myelogenous leukemia (CML), acute monocytic leukemia (AMOL), Hodgkin's lymphomas, Non-Hodgkin's lymphomas, Burkitt's lymphoma (BL), diffuse large B-cell lymphoma (DLBL), Mantle cell lymphoma (MCL), multiple myeloma (MM), and an epithelial malignancy selected from the group consisting of prostate, breast, brain, kidney, lung, colon, bladder, skin, thyroid, ovary tumors, and mesothelioma;

wherein the immunoconjugate further comprises a linker, and the linker comprises a first linking component and a second linking component;

wherein the first linking component comprises PEG and the second linking component comprises PEG;

wherein the first linking component is bound to the second linking component through a triazole moiety, and wherein the cytotoxic agent is bound to the second linking component; and wherein the linker is covalently bound to a lysine residue on the anti-matriptase antibody, wherein the second linking component comprises a cleavable linking moiety which is cleavable by Cathepsin B.

2. The method of claim 1, wherein the cytotoxic agent is monomethyl auristatin E (MMAE).

3. The method of claim 1, wherein the cleavable linking moiety comprises a Val-Cit linking moiety, cleavable by Cathepsin B.

4. The method of claim 1, wherein the cleavable linking moiety comprises a Phe-Lys linking moiety, cleavable by Cathepsin B.

5. The method of claim 1, wherein the first linking component is covalently bound to a lysine residue on the anti-matriptase antibody or the antigen-binding fragment thereof.

6. The method of claim 1, wherein the cleavable linking moiety comprises a Val-Cit linking moiety or a Phe-Lys linking moiety, cleavable by Cathepsin B.

7. The method of claim 1, wherein the cytotoxic agent is bound to the second linking component through the cleavable linking moiety.

8. The method of claim 1, wherein the first linking component comprises between about 3 and about 7 PEG units.

9. The method of claim 1, wherein the second linking component comprises between about 3 and about 7 PEG units.

* * * * *